(12) United States Patent
Chen et al.

(10) Patent No.: US 8,350,023 B2
(45) Date of Patent: Jan. 8, 2013

(54) CRYSTALLINE POLYMORPHS OF GEMCITABINE BASE

(75) Inventors: Shu-Ping Chen, Kaohsiung (TW);
Chia-Lin Charlene Shieh, Kaohsiung (TW)

(73) Assignee: ScnioPharm Taiwan, Ltd., Tainan (TW)

( * ) Notice: Subject to any disclaimer, the term of this patent is extended or adjusted under 35 U.S.C. 154(b) by 758 days.

(21) Appl. No.: 12/483,375

(22) Filed: Jun. 12, 2009

(65) Prior Publication Data

US 2009/0326214 A1    Dec. 31, 2009

Related U.S. Application Data

(60) Provisional application No. 61/131,835, filed on Jun. 12, 2008.

(51) Int. Cl.
*C07H 19/00* (2006.01)

(52) U.S. Cl. .................................................... 536/28.5

(58) Field of Classification Search ........................ None
See application file for complete search history.

(56) References Cited

U.S. PATENT DOCUMENTS

| | | | | |
|---|---|---|---|---|
| 4,808,614 A | * | 2/1989 | Hertel | 514/45 |
| 6,395,300 B1 | * | 5/2002 | Straub et al. | 424/489 |
| 6,645,528 B1 | * | 11/2003 | Straub et al. | 424/489 |
| 6,932,983 B1 | * | 8/2005 | Straub et al. | 424/489 |
| 7,919,119 B2 | * | 4/2011 | Straub et al. | 424/489 |
| 8,114,854 B2 | * | 2/2012 | Oblezov | 514/49 |

FOREIGN PATENT DOCUMENTS

WO    WO2007/0149891    12/2007

OTHER PUBLICATIONS (R) Capdeville et al., "Glivec (STI571, Imatinib), A Rationally Developed, Targeted Anticancer Drug," Nature Reviews Drug Discovery, 1(7), 493-502 (Jul. 2002).*
(S) Hausheer et al., "Ab Initio Quantum Mechanical and X-ray Crystallographic Studies of Gemcitabine and 2'-Deoxycytidine," Computers & Chemistry, 20(4), 459-467 (1996).*
(T) Google search on Mar. 11, 2012: seach term "gemcitabine and melting point:" see first entry when the m.p. and the date Jun. 2005 are disclosed.*
(U) DrugBank: "Gemcitabine" data—see end of p. 3 wherein the Melting Point is disclosed to be 168.64 ° C.: Found with Google Search of Mar. 11, 2012. See p. 8, first of last four lines wherein the date of Jun. 2005 is disclosed.*
International Preliminary Report on Patentability dated Dec. 23, 2010, for PCT/US2009/047190.
Glivec (STI571, Imatinib), A Rationally Developed Targeted Anticancer Drug, *Nature Reviews,* vol. 1, Jul. 2002, p. 493-502; Capdeville et al.

* cited by examiner

*Primary Examiner* — Lawrence E Crane

(57) ABSTRACT

The present application provides several crystalline forms of gemcitabine base and methods of making the same.

24 Claims, 39 Drawing Sheets

File: Untitled1

Comment:

Scan Type: Normal
Start Angle: 2 deg.
Stop Angle: 40 deg.
Num Points: 1901
Step Size: 0.02 deg.
Datafile Res: 1600
Scan Rate: 2.000000
Scan Mode: Continuous
Wavelength: 1.540562

Diffractometer Optics:
  Detector:
    Type: Fixed Slits
    K2 Configuration: No
  Tube:
    Type: Fixed Slits
    K2 Configuration: No Peaks:

| Position (Deg.) | Position (DSp.) | ESD (Deg.) | Corr.Fact | Intensity (cps) | Rel. Int. (%) | FWHM (L) | ESD (Deg.) | Area | Source | Curve | Strain | CSize | CSize Source |
|---|---|---|---|---|---|---|---|---|---|---|---|---|---|
| 5.8119 | 12.9656 | 0.0000 | 0.0000 | 445.35 | 14.86 | 0.1200 | 0.0000 | 71.3 | PFind | None | 0.00 | 0.00 | None |
| 9.3737 | 9.4270 | 0.0000 | 0.0000 | 2358.95 | 78.73 | 0.1600 | 0.0000 | 377.4 | PFind | None | 0.00 | 0.00 | None |
| 9.9400 | 8.8912 | 0.0000 | 0.0000 | 150.00 | 5.01 | 0.0600 | 0.0000 | 6.0 | PFind | None | 0.00 | 0.00 | None |
| 15.7075 | 5.6371 | 0.0000 | 0.0000 | 1346.48 | 44.94 | 0.1600 | 0.0000 | 215.4 | PFind | None | 0.00 | 0.00 | None |
| 16.0781 | 5.5000 | 0.0000 | 0.0000 | 1963.08 | 65.52 | 0.1400 | 0.0000 | 314.1 | PFind | None | 0.00 | 0.00 | None |
| 16.7282 | 5.2954 | 0.0000 | 0.0000 | 1207.28 | 40.29 | 0.1600 | 0.0000 | 193.2 | PFind | None | 0.00 | 0.00 | None |
| 18.8862 | 4.6949 | 0.0000 | 0.0000 | 666.00 | 22.23 | 0.1600 | 0.0000 | 106.6 | PFind | None | 0.00 | 0.00 | None |
| 19.6306 | 4.5185 | 0.0000 | 0.0000 | 725.00 | 24.20 | 0.1600 | 0.0000 | 116.0 | PFind | None | 0.00 | 0.00 | None |
| 19.7306 | 4.4958 | 0.0000 | 0.0000 | 626.85 | 20.92 | 0.1200 | 0.0000 | 75.2 | PFind | None | 0.00 | 0.00 | None |
| 19.9988 | 4.4361 | 0.0000 | 0.0000 | 650.65 | 21.71 | 0.1600 | 0.0000 | 104.1 | PFind | None | 0.00 | 0.00 | None |
| 20.6731 | 4.2929 | 0.0000 | 0.0000 | 1942.30 | 64.82 | 0.1600 | 0.0000 | 310.8 | PFind | None | 0.00 | 0.00 | None |
| 22.1200 | 4.0153 | 0.0000 | 0.0000 | 330.00 | 11.01 | 0.0400 | 0.0000 | 26.4 | PFind | None | 0.00 | 0.00 | None |
| 22.2400 | 3.9939 | 0.0000 | 0.0000 | 305.00 | 10.18 | 0.1600 | 0.0000 | 36.6 | PFind | None | 0.00 | 0.00 | None |
| 22.8194 | 3.8938 | 0.0000 | 0.0000 | 259.12 | 8.65 | 0.1400 | 0.0000 | 31.1 | PFind | None | 0.00 | 0.00 | None |
| 22.9200 | 3.8769 | 0.0000 | 0.0000 | 311.67 | 10.40 | 0.1600 | 0.0000 | 12.5 | PFind | None | 0.00 | 0.00 | None |
| 24.2700 | 3.6642 | 0.0000 | 0.0000 | 1091.53 | 36.43 | 0.1600 | 0.0000 | 174.6 | PFind | None | 0.00 | 0.00 | None |
| 25.5069 | 3.4893 | 0.0000 | 0.0000 | 320.90 | 10.71 | 0.1600 | 0.0000 | 51.3 | PFind | None | 0.00 | 0.00 | None |
| 25.8381 | 3.4453 | 0.0000 | 0.0000 | 456.83 | 15.25 | 0.0800 | 0.0000 | 73.1 | PFind | None | 0.00 | 0.00 | None |
| 27.6150 | 3.2275 | 0.0000 | 0.0000 | 2996.32 | 100.00 | 0.1600 | 0.0000 | 479.4 | PFind | None | 0.00 | 0.00 | None |
| 28.1856 | 3.1635 | 0.0000 | 0.0000 | 210.98 | 7.04 | 0.0500 | 0.0000 | 29.5 | PFind | None | 0.00 | 0.00 | None |
| 28.6600 | 3.1122 | 0.0000 | 0.0000 | 206.67 | 6.90 | 0.0600 | 0.0000 | 12.4 | PFind | None | 0.00 | 0.00 | None |
| 28.9237 | 3.0844 | 0.0000 | 0.0000 | 166.62 | 5.56 | 0.0800 | 0.0000 | 20.0 | PFind | None | 0.00 | 0.00 | None |
| 29.1700 | 3.0589 | 0.0000 | 0.0000 | 213.22 | 7.12 | 0.1200 | 0.0000 | 12.8 | PFind | None | 0.00 | 0.00 | None |
| 31.0600 | 2.8769 | 0.0000 | 0.0000 | 168.33 | 5.62 | 0.1000 | 0.0000 | 16.8 | PFind | None | 0.00 | 0.00 | None |
| 31.6600 | 2.8106 | 0.0000 | 0.0000 | 190.00 | 6.34 | 0.0600 | 0.0000 | 0.0 | PFind | None | 0.00 | 0.00 | None |
| 31.7200 | 2.8089 | 0.0000 | 0.0000 | 240.66 | 8.03 | 0.0600 | 0.0000 | 14.4 | PFind | None | 0.00 | 0.00 | None |
| 31.8319 | 2.7643 | 0.0000 | 0.0000 | 310.00 | 10.35 | 0.1600 | 0.0000 | 24.8 | PFind | None | 0.00 | 0.00 | None |
| 32.3400 | 2.7530 | 0.0000 | 0.0000 | 157.80 | 5.27 | 0.0800 | 0.0000 | 12.6 | PFind | None | 0.00 | 0.00 | None |
| 32.4956 | 2.6093 | 0.0000 | 0.0000 | 199.87 | 6.67 | 0.0300 | 0.0000 | 20.0 | PFind | None | 0.00 | 0.00 | None |
| 34.3400 | 2.4480 | 0.0000 | 0.0000 | 161.67 | 5.40 | 0.1400 | 0.0000 | 12.9 | PFind | None | 0.00 | 0.00 | None |
| 35.6800 | 2.4323 | 0.0000 | 0.0000 | 347.23 | 11.59 | 0.1200 | 0.0000 | 48.6 | PFind | None | 0.00 | 0.00 | None |
| 36.9256 | 2.4137 | 0.0000 | 0.0000 | 188.33 | 6.29 | 0.0800 | 0.0000 | 3.8 | PFind | None | 0.00 | 0.00 | None |
| 37.2200 | 2.3153 | 0.0000 | 0.0000 | 173.33 | 5.78 | 0.0800 | 0.0000 | 13.9 | PFind | None | 0.00 | 0.00 | None |

FIG. 1(a) continued

File: Untitled1

| 39.0544 | 2.3045 | 0.0000 | 0.0000 | 158.55 | 5.29 | 0.0200 | 0.0000 | 9.5 | PFind None | 0.00 | 0.00 | None |

FIG. 1(a) continued

File: Untitled2

Comment:

Scan Type: Normal
Start Angle: 2 deg.
Stop Angle: 40 deg.
Num Points: 1901
Step Size: 0.02 deg.
Datafile Res: 1600
Scan Rate: 2.000000
Scan Mode: Continuous
Wavelength: 1.540562

Diffractometer Optics:
  Detector:
    Type: Fixed Slits
    X2 Configuration: No
  Tube:
    Type: Fixed Slits
    X2 Configuration: No Peaks:

| Position (Deg.) | (DSp.) | ESD (Deg.) | Corr.Fact | Intensity (cps) | Rel. Int. (%) | FWHM (L) | ESD (Deg.) | Area | Source | Curve | Strain | CSize | CSize Source |
|---|---|---|---|---|---|---|---|---|---|---|---|---|---|
| 10.5063 | 8.4132 | 0.0000 | 0.0000 | 1173.68 | 28.86 | 0.1600 | 0.0000 | 187.8 | PFind | None | 0.00 | 0.00 | None |
| 11.7906 | 7.4995 | 0.0000 | 0.0000 | 3016.67 | 74.24 | 0.1600 | 0.0000 | 482.7 | PFind | None | 0.00 | 0.00 | None |
| 12.0225 | 7.3554 | 0.0000 | 0.0000 | 629.17 | 15.48 | 0.1600 | 0.0000 | 100.7 | PFind | None | 0.00 | 0.00 | None |
| 15.8075 | 5.6017 | 0.0000 | 0.0000 | 1558.05 | 38.34 | 0.1400 | 0.0000 | 249.3 | PFind | None | 0.00 | 0.00 | None |
| 17.0944 | 5.1828 | 0.0000 | 0.0000 | 920.33 | 22.65 | 0.1400 | 0.0000 | 147.3 | PFind | None | 0.00 | 0.00 | None |
| 18.1475 | 4.8843 | 0.0000 | 0.0000 | 681.00 | 16.76 | 0.1200 | 0.0000 | 68.1 | PFind | None | 0.00 | 0.00 | None |
| 20.0125 | 4.4331 | 0.0000 | 0.0000 | 605.43 | 14.90 | 0.1200 | 0.0000 | 72.7 | PFind | None | 0.00 | 0.00 | None |
| 20.2463 | 4.3825 | 0.0000 | 0.0000 | 589.68 | 14.51 | 0.1600 | 0.0000 | 92.6 | PFind | None | 0.00 | 0.00 | None |
| 20.8337 | 4.2602 | 0.0000 | 0.0000 | 4063.45 | 100.00 | 0.1600 | 0.0000 | 650.2 | PFind | None | 0.00 | 0.00 | None |
| 21.1169 | 4.2037 | 0.0000 | 0.0000 | 1759.42 | 43.30 | 0.1200 | 0.0000 | 211.1 | PFind | None | 0.00 | 0.00 | None |
| 21.9644 | 4.0434 | 0.0000 | 0.0000 | 1393.60 | 34.30 | 0.1600 | 0.0000 | 223.0 | PFind | None | 0.00 | 0.00 | None |
| 23.5056 | 3.7816 | 0.0000 | 0.0000 | 3966.58 | 97.62 | 0.1600 | 0.0000 | 634.7 | PFind | None | 0.00 | 0.00 | None |
| 24.3044 | 3.6591 | 0.0000 | 0.0000 | 724.08 | 17.82 | 0.1400 | 0.0000 | 101.4 | PFind | None | 0.00 | 0.00 | None |
| 24.7600 | 3.5928 | 0.0000 | 0.0000 | 914.28 | 22.50 | 0.1600 | 0.0000 | 146.3 | PFind | None | 0.00 | 0.00 | None |
| 27.0981 | 3.2879 | 0.0000 | 0.0000 | 380.95 | 9.38 | 0.1200 | 0.0000 | 45.7 | PFind | None | 0.00 | 0.00 | None |
| 27.5569 | 3.2342 | 0.0000 | 0.0000 | 1847.17 | 45.46 | 0.1000 | 0.0000 | 295.5 | PFind | None | 0.00 | 0.00 | None |
| 27.7738 | 3.2094 | 0.0000 | 0.0000 | 2550.00 | 62.75 | 0.1200 | 0.0000 | 357.0 | PFind | None | 0.00 | 0.00 | None |
| 28.1863 | 3.1634 | 0.0000 | 0.0000 | 1340.28 | 32.98 | 0.1600 | 0.0000 | 187.6 | PFind | None | 0.00 | 0.00 | None |
| 30.0675 | 2.9696 | 0.0000 | 0.0000 | 2520.07 | 62.02 | 0.1600 | 0.0000 | 403.2 | PFind | None | 0.00 | 0.00 | None |
| 31.7062 | 2.8198 | 0.0000 | 0.0000 | 605.53 | 14.90 | 0.1600 | 0.0000 | 96.9 | PFind | None | 0.00 | 0.00 | None |
| 32.0231 | 2.7926 | 0.0000 | 0.0000 | 581.63 | 14.31 | 0.1600 | 0.0000 | 69.8 | PFind | None | 0.00 | 0.00 | None |
| 32.5613 | 2.7495 | 0.0000 | 0.0000 | 537.02 | 13.22 | 0.1600 | 0.0000 | 75.2 | PFind | None | 0.00 | 0.00 | None |
| 32.7150 | 2.7380 | 0.0000 | 0.0000 | 1384.73 | 34.08 | 0.1200 | 0.0000 | 221.6 | PFind | None | 0.00 | 0.00 | None |
| 32.9644 | 2.7178 | 0.0000 | 0.0000 | 358.83 | 8.83 | 0.1600 | 0.0000 | 57.4 | PFind | None | 0.00 | 0.00 | None |
| 34.2075 | 2.6191 | 0.0000 | 0.0000 | 605.27 | 14.90 | 0.1400 | 0.0000 | 96.8 | PFind | None | 0.00 | 0.00 | None |
| 36.0112 | 2.4919 | 0.0000 | 0.0000 | 687.10 | 16.91 | 0.1600 | 0.0000 | 109.9 | PFind | None | 0.00 | 0.00 | None |
| 36.2319 | 2.4773 | 0.0000 | 0.0000 | 653.28 | 16.08 | 0.1400 | 0.0000 | 78.4 | PFind | None | 0.00 | 0.00 | None |
| 36.7375 | 2.4443 | 0.0000 | 0.0000 | 440.27 | 10.83 | 0.1600 | 0.0000 | 70.4 | PFind | None | 0.00 | 0.00 | None |
| 38.3150 | 2.3472 | 0.0000 | 0.0000 | | | | | | | | | | |

FIG. 2(a) continued

File: Untitled3

Comment:

Scan Type: Normal
Start Angle: 2 deg.
Stop Angle: 40 deg.
Num Points: 1901
Step Size: 0.02 deg.
Datafile Res: 1600
Scan Rate: 2.000000
Scan Mode: Continuous
Wavelength: 1.540562

Diffractometer Optics:
  Detector:
    Type: Fixed Slits
    X2 Configuration: No
  Tube:
    Type: Fixed Slits
    X2 Configuration: No Peaks:

| Position (Deg.) | (DSp.) | ESD (Deg.) | Corr.Fact | Intensity (cps) | Rel. Int. (%) | FWHM (L) | ESD (Deg.) | Area | Source | Curve | Strain | CSize | CSize Source |
|---|---|---|---|---|---|---|---|---|---|---|---|---|---|
| 12.0569 | 7.3345 | 0.0000 | 0.0000 | 1064.97 | 18.51 | 0.1400 | 0.0000 | 170.4 | PFind | None | 0.00 | 0.00 | None |
| 14.3881 | 6.1509 | 0.0000 | 0.0000 | 3342.32 | 58.08 | 0.1400 | 0.0000 | 534.8 | PFind | None | 0.00 | 0.00 | None |
| 15.6743 | 5.6743 | 0.0000 | 0.0000 | 4717.67 | 81.98 | 0.1600 | 0.0000 | 754.8 | PFind | None | 0.00 | 0.00 | None |
| 18.8438 | 4.7054 | 0.0000 | 0.0000 | 1693.23 | 29.42 | 0.1400 | 0.0000 | 237.0 | PFind | None | 0.00 | 0.00 | None |
| 19.3706 | 4.5786 | 0.0000 | 0.0000 | 478.22 | 8.31 | 0.1400 | 0.0000 | 76.5 | PFind | None | 0.00 | 0.00 | None |
| 22.3025 | 3.9828 | 0.0000 | 0.0000 | 5754.55 | 100.00 | 0.1600 | 0.0000 | 805.6 | PFind | None | 0.00 | 0.00 | None |
| 22.9994 | 3.8637 | 0.0000 | 0.0000 | 1735.65 | 30.16 | 0.1500 | 0.0000 | 277.7 | PFind | None | 0.00 | 0.00 | None |
| 23.5737 | 3.7709 | 0.0000 | 0.0000 | 2953.33 | 51.32 | 0.1600 | 0.0000 | 413.5 | PFind | None | 0.00 | 0.00 | None |
| 24.3544 | 3.6517 | 0.0000 | 0.0000 | 3477.50 | 60.43 | 0.1600 | 0.0000 | 556.4 | PFind | None | 0.00 | 0.00 | None |
| 24.5800 | 3.6187 | 0.0000 | 0.0000 | 433.58 | 7.53 | 0.1200 | 0.0000 | 54.7 | PFind | None | 0.00 | 0.00 | None |
| 25.3475 | 3.5109 | 0.0000 | 0.0000 | 819.65 | 14.24 | 0.1200 | 0.0000 | 114.8 | PFind | None | 0.00 | 0.00 | None |
| 28.3906 | 3.1411 | 0.0000 | 0.0000 | 545.00 | 9.47 | 0.1200 | 0.0000 | 87.2 | PFind | None | 0.00 | 0.00 | None |
| 29.0894 | 3.0672 | 0.0000 | 0.0000 | 1448.27 | 25.17 | 0.1600 | 0.0000 | 231.7 | PFind | None | 0.00 | 0.00 | None |
| 29.7231 | 3.0032 | 0.0000 | 0.0000 | 448.93 | 7.80 | 0.1600 | 0.0000 | 71.8 | PFind | None | 0.00 | 0.00 | None |
| 32.4550 | 2.7564 | 0.0000 | 0.0000 | 572.22 | 9.94 | 0.1600 | 0.0000 | 68.7 | PFind | None | 0.00 | 0.00 | None |
| 33.7006 | 2.6573 | 0.0000 | 0.0000 | 523.33 | 9.09 | 0.1600 | 0.0000 | 83.7 | PFind | None | 0.00 | 0.00 | None |
| 33.9375 | 2.6393 | 0.0000 | 0.0000 | 851.05 | 14.79 | 0.1600 | 0.0000 | 119.1 | PFind | None | 0.00 | 0.00 | None |
| 34.5231 | 2.5959 | 0.0000 | 0.0000 | 2468.97 | 42.90 | 0.1400 | 0.0000 | 395.0 | PFind | None | 0.00 | 0.00 | None |
| 34.7562 | 2.5790 | 0.0000 | 0.0000 | 1265.90 | 22.00 | 0.0800 | 0.0000 | 151.9 | PFind | None | 0.00 | 0.00 | None |
| 36.8056 | 2.4348 | 0.0000 | 0.0000 | 343.10 | 5.96 | 0.1200 | 0.0000 | 41.2 | PFind | None | 0.00 | 0.00 | None |
| 39.6606 | 2.3270 | 0.0000 | 0.0000 | 315.98 | 5.49 | 0.1600 | 0.0000 | 50.6 | PFind | None | 0.00 | 0.00 | None |

FIG. 3(a) continued

File: Untitled4

Comment:

Scan Type: Normal
Start Angle: 2 deg.
Stop Angle: 40 deg.
Num Points: 1901
Step Size: 0.02 deg.
Datafile Res: 1600
Scan Rate: 2.000000
Scan Mode: Continuous
Wavelength: 1.540562

Diffractometer Optics:
  Detector:
    Type: Fixed Slits
    X2 Configuration: No
  Tube:
    Type: Fixed Slits
    X2 Configuration: No Peaks:

| Position (Deg.) | DSp. (Deg.) | ESD (Deg.) | Corr.Fact | Intensity (cps) | Rel. Int. (%) | FWHM (L) | ESD (Deg.) | Area | Source | Curve | Strain | CSize | CSize Source |
|---|---|---|---|---|---|---|---|---|---|---|---|---|---|
| 10.1237 | 8.7302 | 0.0000 | 0.0000 | 841.42 | 26.16 | 0.1600 | 0.0000 | 134.6 | PFind | None | 0.00 | 0.00 | None |
| 10.5981 | 8.3405 | 0.0000 | 0.0000 | 1445.22 | 44.92 | 0.1000 | 0.0000 | 144.5 | PFind | None | 0.00 | 0.00 | None |
| 11.8294 | 7.4750 | 0.0000 | 0.0000 | 351.40 | 10.92 | 0.1600 | 0.0000 | 35.1 | PFind | None | 0.00 | 0.00 | None |
| 12.2200 | 7.2487 | 0.0000 | 0.0000 | 355.00 | 11.04 | 0.1600 | 0.0000 | 35.5 | PFind | None | 0.00 | 0.00 | None |
| 14.0619 | 6.2929 | 0.0000 | 0.0000 | 3217.02 | 100.00 | 0.1600 | 0.0000 | 514.7 | PFind | None | 0.00 | 0.00 | None |
| 14.9412 | 5.9240 | 0.0000 | 0.0000 | 1268.65 | 39.44 | 0.1600 | 0.0000 | 203.0 | PFind | None | 0.00 | 0.00 | None |
| 15.9487 | 5.5524 | 0.0000 | 0.0000 | 616.55 | 19.17 | 0.1400 | 0.0000 | 86.3 | PFind | None | 0.00 | 0.00 | None |
| 16.2198 | 5.4605 | 0.0000 | 0.0000 | 470.88 | 14.64 | 0.1400 | 0.0000 | 65.9 | PFind | None | 0.00 | 0.00 | None |
| 16.8800 | 5.2481 | 0.0000 | 0.0000 | 323.33 | 10.05 | 0.0600 | 0.0000 | 38.8 | PFind | None | 0.00 | 0.00 | None |
| 16.9600 | 5.2235 | 0.0000 | 0.0000 | 338.33 | 9.58 | 0.0800 | 0.0000 | 49.3 | PFind | None | 0.00 | 0.00 | None |
| 17.3025 | 5.1209 | 0.0000 | 0.0000 | 871.98 | 27.11 | 0.1600 | 0.0000 | 139.5 | PFind | None | 0.00 | 0.00 | None |
| 19.0339 | 4.6568 | 0.0000 | 0.0000 | 824.40 | 25.63 | 0.1600 | 0.0000 | 131.9 | PFind | None | 0.00 | 0.00 | None |
| 19.7131 | 4.4998 | 0.0000 | 0.0000 | 623.55 | 19.38 | 0.1600 | 0.0000 | 99.8 | PFind | None | 0.00 | 0.00 | None |
| 20.6606 | 4.2955 | 0.0000 | 0.0000 | 2468.15 | 76.72 | 0.1600 | 0.0000 | 394.9 | PFind | None | 0.00 | 0.00 | None |
| 21.2331 | 4.1810 | 0.0000 | 0.0000 | 466.63 | 14.51 | 0.1000 | 0.0000 | 74.7 | PFind | None | 0.00 | 0.00 | None |
| 22.1688 | 4.0066 | 0.0000 | 0.0000 | 1001.13 | 31.12 | 0.1400 | 0.0000 | 100.1 | PFind | None | 0.00 | 0.00 | None |
| 22.9862 | 3.8659 | 0.0000 | 0.0000 | 977.67 | 30.39 | 0.1200 | 0.0000 | 156.4 | PFind | None | 0.00 | 0.00 | None |
| 23.6525 | 3.7585 | 0.0000 | 0.0000 | 263.35 | 8.19 | 0.1600 | 0.0000 | 15.8 | PFind | None | 0.00 | 0.00 | None |
| 24.4206 | 3.6420 | 0.0000 | 0.0000 | 1398.69 | 43.48 | 0.1000 | 0.0000 | 111.9 | PFind | None | 0.00 | 0.00 | None |
| 24.5975 | 3.6162 | 0.0000 | 0.0000 | 270.70 | 8.41 | 0.1000 | 0.0000 | 16.2 | PFind | None | 0.00 | 0.00 | None |
| 26.9806 | 3.3019 | 0.0000 | 0.0000 | 703.77 | 21.88 | 0.1600 | 0.0000 | 112.5 | PFind | None | 0.00 | 0.00 | None |
| 27.7600 | 3.2110 | 0.0000 | 0.0000 | 1431.33 | 44.49 | 0.1600 | 0.0000 | 229.0 | PFind | None | 0.00 | 0.00 | None |
| 29.0731 | 3.0689 | 0.0000 | 0.0000 | 399.58 | 12.42 | 0.1000 | 0.0000 | 55.9 | PFind | None | 0.00 | 0.00 | None |
| 30.2213 | 2.9453 | 0.0030 | 0.0030 | 1415.72 | 44.01 | 0.1600 | 0.0000 | 226.5 | PFind | None | 0.00 | 0.00 | None |
| 31.7125 | 2.8192 | 0.0000 | 0.0000 | 359.40 | 11.17 | 0.1600 | 0.0000 | 57.5 | PFind | None | 0.00 | 0.00 | None |
| 31.8481 | 2.8075 | 0.0000 | 0.0000 | 490.00 | 15.23 | 0.1600 | 0.0000 | 78.4 | PFind | None | 0.00 | 0.00 | None |
| 32.1569 | 2.7813 | 0.0000 | 0.0000 | 820.17 | 25.49 | 0.1600 | 0.0000 | 131.2 | PFind | None | 0.100 | 0.00 | None |
| 33.0831 | 2.7055 | 0.0000 | 0.0000 | 399.42 | 12.10 | 0.1600 | 0.0000 | 31.2 | PFind | None | 0.00 | 0.00 | None |
| 34.3706 | 2.6070 | 0.0000 | 0.0000 | 422.67 | 13.14 | 0.0500 | 0.0000 | 25.4 | PFind | None | 0.00 | 0.00 | None |
| 36.0369 | 2.4902 | 0.0000 | 0.0000 | 334.10 | 11.94 | 0.1400 | 0.0000 | 38.4 | PFind | None | 0.00 | 0.00 | None |
| 38.5200 | 2.3352 | 0.0000 | 0.0000 | 239.45 | 9.00 | 0.0600 | 0.0000 | 46.3 | PFind | None | 0.00 | 0.00 | None |

FIG. 4(a) continued

Page:1

File: Untitled6

Comment:

Scan Type: Normal
Start Angle: 2 deg.
Stop Angle: 40 deg.
Num Points: 1901
Step Size: 0.02 deg.
Datafile Res: 1600
Scan Rate: 2.000000
Scan Mode: Continuous
Wavelength: 1.540562

Diffractometer Optics:
 Detector:
  Type: Fixed Slits
  X2 Configuration: No
 Tube:
  Type: Fixed Slits
  X2 Configuration: No Peaks:

| Position (Deg.) | (DSp.) | ESD (Deg.) | Corr.Fact | Intensity (cps) | Rel. Int. (%) | FWHM (L) | ESD (Deg.) | Area | Source | Curve | Strain | CSize | CSize Source |
|---|---|---|---|---|---|---|---|---|---|---|---|---|---|
| 9.3400 | 9.4610 | 0.0000 | 0.0000 | 245.00 | 7.09 | 0.0800 | 0.0000 | 9.8 | PFind | None | 0.00 | 0.00 | None |
| 10.3400 | 8.5481 | 0.0000 | 0.0000 | 2120.00 | 61.34 | 0.1600 | 0.0000 | 84.8 | PFind | None | 0.00 | 0.00 | None |
| 10.4619 | 8.4488 | 0.0000 | 0.0000 | 1662.00 | 48.09 | 0.1000 | 0.0000 | 166.2 | PFind | None | 0.00 | 0.00 | None |
| 11.7550 | 7.5221 | 0.0000 | 0.0000 | 3085.50 | 89.28 | 0.1000 | 0.0000 | 370.3 | PFind | None | 0.00 | 0.00 | None |
| 12.0000 | 7.3691 | 0.0000 | 0.0000 | 790.07 | 22.86 | 0.1200 | 0.0000 | 94.8 | PFind | None | 0.00 | 0.00 | None |
| 15.7675 | 5.6158 | 0.0000 | 0.0000 | 1528.27 | 44.22 | 0.1200 | 0.0000 | 214.0 | PFind | None | 0.00 | 0.00 | None |
| 16.0462 | 5.5188 | 0.0000 | 0.0000 | 230.50 | 8.41 | 0.1600 | 0.0000 | 46.5 | PFind | None | 0.00 | 0.00 | None |
| 16.7162 | 5.2991 | 0.0000 | 0.0000 | 287.75 | 8.33 | 0.1600 | 0.0000 | 28.8 | PFind | None | 0.00 | 0.00 | None |
| 17.0219 | 5.2047 | 0.0000 | 0.0000 | 644.65 | 18.65 | 0.0400 | 0.0000 | 90.3 | PFind | None | 0.00 | 0.00 | None |
| 18.0594 | 4.9079 | 0.0000 | 0.0000 | 425.25 | 12.30 | 0.1200 | 0.0000 | 51.0 | PFind | None | 0.00 | 0.00 | None |
| 19.9925 | 4.4375 | 0.0000 | 0.0000 | 404.88 | 11.71 | 0.1000 | 0.0000 | 40.5 | PFind | None | 0.00 | 0.00 | None |
| 20.2475 | 4.3822 | 0.0000 | 0.0000 | 595.60 | 17.23 | 0.1600 | 0.0000 | 71.5 | PFind | None | 0.00 | 0.00 | None |
| 20.8294 | 4.2611 | 0.0000 | 0.0000 | 3186.98 | 92.21 | 0.1600 | 0.0000 | 509.9 | PFind | None | 0.00 | 0.00 | None |
| 21.9713 | 4.0421 | 0.0000 | 0.0000 | 1572.17 | 45.49 | 0.0400 | 0.0000 | 125.8 | PFind | None | 0.00 | 0.00 | None |
| 23.4944 | 3.7834 | 0.0000 | 0.0000 | 3456.13 | 100.00 | 0.1400 | 0.0000 | 414.7 | PFind | None | 0.00 | 0.00 | None |
| 24.2750 | 3.6635 | 0.0000 | 0.0000 | 894.45 | 25.88 | 0.0800 | 0.0000 | 125.2 | PFind | None | 0.00 | 0.00 | None |
| 24.5331 | 3.6255 | 0.0000 | 0.0000 | 598.55 | 17.32 | 0.0400 | 0.0000 | 59.9 | PFind | None | 0.00 | 0.00 | None |
| 24.7094 | 3.6001 | 0.0000 | 0.0000 | 1129.28 | 32.67 | 0.1200 | 0.0000 | 112.9 | PFind | None | 0.00 | 0.00 | None |
| 26.0200 | 3.4216 | 0.0000 | 0.0000 | 249.33 | 7.29 | 0.1400 | 0.0000 | 9.9 | PFind | None | 0.00 | 0.00 | None |
| 27.0788 | 3.2902 | 0.0000 | 0.0000 | 418.33 | 12.10 | 0.1600 | 0.0000 | 58.6 | PFind | None | 0.00 | 0.00 | None |
| 27.4906 | 3.2418 | 0.0000 | 0.0000 | 2188.77 | 63.33 | 0.1400 | 0.0000 | 350.2 | PFind | None | 0.00 | 0.00 | None |
| 27.7431 | 3.2129 | 0.0000 | 0.0000 | 2375.08 | 68.72 | 0.1200 | 0.0000 | 390.0 | PFind | None | 0.00 | 0.00 | None |
| 28.1494 | 3.1674 | 0.0000 | 0.0000 | 1406.48 | 40.70 | 0.1000 | 0.0000 | 140.6 | PFind | None | 0.00 | 0.00 | None |
| 30.0008 | 2.9753 | 0.0000 | 0.0000 | 2597.12 | 75.15 | 0.1200 | 0.0000 | 363.6 | PFind | None | 0.00 | 0.00 | None |
| 31.5200 | 2.8360 | 0.0000 | 0.0000 | 330.00 | 9.55 | 0.1200 | 0.0000 | 26.4 | PFind | None | 0.00 | 0.00 | None |
| 31.7038 | 2.8200 | 0.0000 | 0.0000 | 651.15 | 18.84 | 0.1200 | 0.0000 | 78.1 | PFind | None | 0.00 | 0.00 | None |
| 31.9813 | 2.7961 | 0.0000 | 0.0000 | 381.67 | 11.04 | 0.1600 | 0.0000 | 61.1 | PFind | None | 0.00 | 0.00 | None |
| 32.6719 | 2.7386 | 0.0000 | 0.0000 | 641.88 | 18.57 | 0.1600 | 0.0000 | 102.7 | PFind | None | 0.00 | 0.00 | None |
| 32.9619 | 2.7152 | 0.0000 | 0.0000 | 1028.77 | 29.77 | 0.1400 | 0.0000 | 102.9 | PFind | None | 0.00 | 0.00 | None |
| 34.2100 | 2.6189 | 0.0000 | 0.0000 | 477.03 | 13.80 | 0.0800 | 0.0000 | 57.2 | PFind | None | 0.00 | 0.00 | None |
| 35.1587 | 2.5504 | 0.0000 | 0.0000 | 411.40 | 11.90 | 0.1600 | 0.0000 | 49.4 | PFind | None | 0.00 | 0.00 | None |
| 35.9253 | 2.4976 | 0.0000 | 0.0000 | 488.97 | 14.15 | 0.1400 | 0.0000 | 58.7 | PFind | None | 0.00 | 0.00 | None |
| 36.1944 | 2.4797 | 0.0000 | 0.0000 | 539.05 | 15.60 | 0.1000 | 0.0000 | 36.2 | PFind | None | 0.00 | 0.00 | None |

FIG. 5(a) continued

| File:Untitled6 | | | | | | | | | | |
|---|---|---|---|---|---|---|---|---|---|---|
| 36.7156 | 2.4457 | 0.0000 | 0.0000 | 698.03 | 20.20 | 0.1400 | 0.0000 | 97.7 | PFind None | 0.00 0.00 None |
| 37.2400 | 2.4125 | 0.0000 | 0.0000 | 276.85 | 8.01 | 0.1400 | 0.0000 | 38.8 | PFind None | 0.00 0.00 None |
| 38.3312 | 2.3463 | 0.0000 | 0.0000 | 665.42 | 19.25 | 0.1000 | 0.0000 | 53.2 | PFind None | 0.00 0.00 None |

FIG. 5(a) continued

File: Untitled5

Comment:

Scan Type: Normal
Start Angle: 2 deg.
Stop Angle: 40 deg.
Num Points: 1901
Step Size: 0.02 deg.
Datafile Res: 1600
Scan Rate: 2.000000
Scan Mode: Continuous
Wavelength: 1.540562

Diffractometer Optics:
  Detector:
    Type: Fixed Slits
    X2 Configuration: No
  Tube:
    Type: Fixed Slits
    X2 Configuration: No Peaks:

| Position (Deg.) | (DSp.) | ESD (Deg.) | Corr.Fact | Intensity (cps) | Rel. Int. (%) | FWHM (L) | ESD (Deg.) | Area | Source | Curve | Strain | CSize | CSize Source |
|---|---|---|---|---|---|---|---|---|---|---|---|---|---|
| 6.8394 | 12.9135 | 0.0000 | 0.0000 | 258.72 | 9.06 | 0.1200 | 0.0000 | 25.9 | PFind | None | 0.00 | 0.00 | None |
| 9.4144 | 9.3864 | 0.0000 | 0.0000 | 1444.47 | 50.60 | 0.1400 | 0.0000 | 231.1 | PFind | None | 0.00 | 0.00 | None |
| 10.5069 | 8.4127 | 0.0000 | 0.0000 | 528.38 | 18.51 | 0.1600 | 0.0000 | 63.4 | PFind | None | 0.00 | 0.00 | None |
| 11.7606 | 7.5186 | 0.0000 | 0.0000 | 1633.15 | 57.21 | 0.1600 | 0.0000 | 261.3 | PFind | None | 0.00 | 0.00 | None |
| 14.3631 | 6.1616 | 0.0000 | 0.0000 | 99.20 | 3.47 | 0.0400 | 0.0000 | 13.9 | PFind | None | 0.00 | 0.00 | None |
| 15.8200 | 5.5973 | 0.0000 | 0.0000 | 1379.47 | 48.32 | 0.1600 | 0.0000 | 220.7 | PFind | None | 0.00 | 0.00 | None |
| 16.0938 | 5.5027 | 0.0000 | 0.0000 | 1307.78 | 45.81 | 0.1600 | 0.0000 | 209.2 | PFind | None | 0.00 | 0.00 | None |
| 16.7956 | 5.2743 | 0.0000 | 0.0000 | 1087.02 | 38.08 | 0.0600 | 0.0000 | 173.9 | PFind | None | 0.00 | 0.00 | None |
| 17.0800 | 5.1871 | 0.0000 | 0.0000 | 355.46 | 12.45 | 0.1600 | 0.0000 | 56.9 | PFind | None | 0.00 | 0.00 | None |
| 18.1000 | 4.8970 | 0.0000 | 0.0000 | 153.33 | 5.37 | 0.1600 | 0.0000 | 9.2 | PFind | None | 0.00 | 0.00 | None |
| 18.3000 | 4.7262 | 0.0000 | 0.0000 | 436.67 | 15.30 | 0.1600 | 0.0000 | 69.9 | PFind | None | 0.00 | 0.00 | None |
| 18.9281 | 4.6846 | 0.0000 | 0.0000 | 350.05 | 12.26 | 0.0800 | 0.0000 | 56.0 | PFind | None | 0.00 | 0.00 | None |
| 19.6925 | 4.5044 | 0.0000 | 0.0000 | 543.90 | 19.05 | 0.1600 | 0.0000 | 87.0 | PFind | None | 0.00 | 0.00 | None |
| 20.0861 | 4.4166 | 0.0000 | 0.0000 | 503.88 | 17.65 | 0.1600 | 0.0000 | 60.5 | PFind | None | 0.00 | 0.00 | None |
| 20.2981 | 4.3714 | 0.0000 | 0.0000 | 226.57 | 7.94 | 0.1600 | 0.0000 | 36.3 | PFind | None | 0.00 | 0.00 | None |
| 20.7512 | 4.2769 | 0.0000 | 0.0000 | 2419.58 | 84.75 | 0.1600 | 0.0000 | 387.1 | PFind | None | 0.00 | 0.00 | None |
| 21.9813 | 4.0403 | 0.0030 | 0.0000 | 715.00 | 25.04 | 0.1600 | 0.0000 | 103.1 | PFind | None | 0.00 | 0.00 | None |
| 22.8900 | 3.8971 | 0.0000 | 0.0000 | 273.33 | 9.57 | 0.0800 | 0.0000 | 21.9 | PFind | None | 0.00 | 0.00 | None |
| 23.5125 | 3.7805 | 0.0000 | 0.0000 | 1809.88 | 63.40 | 0.1200 | 0.0000 | 289.6 | PFind | None | 0.00 | 0.00 | None |
| 24.2844 | 3.6621 | 0.0000 | 0.0000 | 1283.33 | 44.95 | 0.1600 | 0.0000 | 205.3 | PFind | None | 0.00 | 0.00 | None |
| 24.7600 | 3.5928 | 0.0000 | 0.0000 | 371.82 | 13.02 | 0.1600 | 0.0000 | 59.5 | PFind | None | 0.00 | 0.00 | None |
| 25.4394 | 3.4984 | 0.0000 | 0.0000 | 227.15 | 7.96 | 0.0200 | 0.0000 | 27.3 | PFind | None | 0.00 | 0.00 | None |
| 25.8469 | 3.4442 | 0.0000 | 0.0000 | 317.28 | 11.11 | 0.1200 | 0.0000 | 50.8 | PFind | None | 0.00 | 0.00 | None |
| 26.9400 | 3.3068 | 0.0000 | 0.0000 | 156.67 | 5.49 | 0.0200 | 0.0000 | 0.0 | PFind | None | 0.00 | 0.00 | None |
| 27.6294 | 3.2259 | 0.0000 | 0.0000 | 2854.90 | 100.00 | 0.1000 | 0.0000 | 456.8 | PFind | None | 0.00 | 0.00 | None |
| 28.2113 | 3.1606 | 0.0000 | 0.0000 | 620.97 | 21.75 | 0.1600 | 0.0000 | 74.5 | PFind | None | 0.00 | 0.00 | None |
| 28.8337 | 3.0938 | 0.0000 | 0.0000 | 102.92 | 3.60 | 0.0000 | 0.0000 | 8.2 | PFind | None | 0.00 | 0.00 | None |
| 29.0719 | 3.0693 | 0.0000 | 0.0000 | 135.12 | 4.73 | 0.1600 | 0.0000 | 16.2 | PFind | None | 0.00 | 0.00 | None |
| 29.2337 | 3.0524 | 0.0000 | 0.0000 | 105.17 | 3.68 | 0.0200 | 0.0000 | 6.3 | PFind | None | 0.00 | 0.00 | None |
| 30.0656 | 2.9698 | 0.0000 | 0.0000 | 1341.02 | 46.97 | 0.1600 | 0.0000 | 160.9 | PFind | None | 0.00 | 0.00 | None |
| 30.9600 | 2.8860 | 0.0000 | 0.0000 | 143.33 | 5.02 | 0.0400 | 0.0000 | 2.9 | PFind | None | 0.00 | 0.00 | None |
| 31.7294 | 2.8178 | 0.0000 | 0.0000 | 448.30 | 15.70 | 0.1400 | 0.0000 | 71.7 | PFind | None | 0.00 | 0.00 | None |
| 31.9519 | 2.7986 | 0.0000 | 0.0000 | 287.62 | 13.07 | 0.1600 | 0.0000 | 40.3 | PFind | None | 0.00 | 0.00 | None |

Page 1

FIG. 6(a) continued

| File: Untitled5 | | | | | | | | |
|---|---|---|---|---|---|---|---|---|
| 32.2400 | 2.7743 | 0.0000 | 0.0000 | 181.67 | 6.36 | 0.0800 | 0.0000 | 3.6 | PFind None | 0.00 | 0.00 | None |
| 32.3556 | 2.7646 | 0.0000 | 0.0000 | 191.08 | 6.69 | 0.1200 | 0.0000 | 22.9 | PFind None | 0.00 | 0.00 | None |
| 32.9767 | 2.7138 | 0.0000 | 0.0000 | 687.22 | 24.07 | 0.1600 | 0.0000 | 82.5 | PFind None | 0.00 | 0.00 | None |
| 34.2706 | 2.6144 | 0.0000 | 0.0000 | 274.83 | 9.63 | 0.1200 | 0.0000 | 22.0 | PFind None | 0.00 | 0.00 | None |
| 35.9944 | 2.4931 | 0.0000 | 0.0000 | 279.02 | 9.77 | 0.1600 | 0.0000 | 44.6 | PFind None | 0.00 | 0.00 | None |
| 36.3200 | 2.4725 | 0.0000 | 0.0000 | 183.33 | 6.42 | 0.1200 | 0.0000 | 18.3 | PFind None | 0.00 | 0.00 | None |
| 36.4600 | 2.4623 | 0.0000 | 0.0000 | 215.00 | 7.53 | 0.1400 | 0.0000 | 4.3 | PFind None | 0.00 | 0.00 | None |
| 36.7137 | 2.4458 | 0.0000 | 0.0000 | 257.60 | 9.02 | 0.0600 | 0.0000 | 41.2 | PFind None | 0.00 | 0.00 | None |
| 36.8800 | 2.4352 | 0.0000 | 0.0000 | 280.00 | 9.81 | 0.0000 | 0.0000 | 11.2 | PFind None | 0.00 | 0.00 | None |
| 37.2831 | 2.4098 | 0.0000 | 0.0000 | 227.58 | 7.97 | 0.1200 | 0.0000 | 36.4 | PFind None | 0.00 | 0.00 | None |
| 37.5200 | 2.3951 | 0.0000 | 0.0000 | 166.67 | 5.84 | 0.1600 | 0.0000 | 16.7 | PFind None | 0.00 | 0.00 | None |
| 38.2800 | 2.3493 | 0.0000 | 0.0000 | 156.67 | 5.49 | 0.1000 | 0.0000 | 3.1 | PFind None | 0.00 | 0.00 | None |
| 38.7800 | 2.3201 | 0.0000 | 0.0000 | 135.00 | 4.73 | 0.1000 | 0.0000 | 0.0 | PFind None | 0.00 | 0.00 | None |
| 39.0200 | 2.3064 | 0.0000 | 0.0000 | 195.00 | 6.83 | 0.0200 | 0.0000 | 7.8 | PFind None | 0.00 | 0.00 | None |

FIG. 6(a) continued

CRYSTALLINE POLYMORPHS OF GEMCITABINE BASE

RELATED APPLICATIONS

This application claims priority from U.S. Provisional Patent Application Ser. No. 61/131,835 which was filed on Jun. 12, 2008.

BACKGROUND OF THE INVENTION

1. Field of the Invention

The present application relates to crystalline forms of gemcitabine base, as well as processes for the preparation thereof.

2. Description of the Related Art

Gemcitabine is a nucleoside analog used as chemotherapy. Gemcitabine has the following structure:

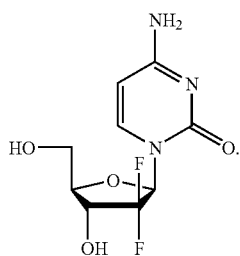

Its chemical name is 4-amino-1-[3,3-difluoro-4-hydroxy-5-(hydroxymethyl) tetrahydrofuran-2-yl]-1H-pyrimidin-2-one, chemical formula is: $C_9H_{11}F_2N_3O_4$; molecular weight is 263.198 g/mol.

The discovery of new polymorphic forms of a pharmaceutically useful compound provides a new opportunity to improve the performance characteristics of a pharmaceutical product. It enlarges the repertoire of materials that a formulation scientist has available for designing, for example, a pharmaceutical dosage form of a drug with a targeted release profile or other desired characteristic.

There is a need in the art for various polymorphic forms of gemcitabine.

SUMMARY OF THE INVENTION

The present application provides several crystalline forms of gemcitabine base, i.e., Forms A-F.

In accordance with one embodiment, crystalline Form A of gemcitabine base is characterized by a powder x-ray diffraction pattern with peaks at about 27.6 and 9.4±0.2 degrees two-theta; preferably, Form A is further characterized by a powder x-ray diffraction pattern with peaks at about 16.1 and 20.7±0.2 degrees two-theta; more preferably, Form A is further characterized by a powder x-ray diffraction pattern with peaks at about 6.8, 15.7, 16.7, and 24.3±0.2 degrees two-theta. As a preferred embodiment, crystalline Form A is further characterized by a powder x-ray diffraction pattern as depicted in FIG. 1(a).

Preferably, crystalline Form A of claim 1 is further characterized by a DSC thermogram as depicted in FIG. 1(b).

Preferably, the crystalline Form A is further characterized by an infrared spectrum having bands at about 781, 1094, 1523, 1660, 1696, and 3404 (cm$^{-1}$). More preferably, crystalline Form A is further characterized by an infrared spectrum as depicted in FIG. 1(c).

In accordance with another embodiment, crystalline Form B of gemcitabine base is characterized by a powder x-ray diffraction pattern with peaks at about 20.8 and 23.5±0.2 degrees two-theta; preferably, crystalline Form B is further characterized by a powder x-ray diffraction pattern with peaks at about 11.8, 27.8, and 30.1±0.2 degrees two-theta; more preferably, crystalline Form B is further characterized by a powder x-ray diffraction pattern with peaks at about 10.5, 15.8, 22.0, and 33.0±0.2 degrees two-theta. As a preferred embodiment, crystalline Form B is further characterized by a powder x-ray diffraction pattern as depicted in FIG. 2(a).

Preferably, crystalline Form B is characterized by a DSC thermogram as depicted in FIG. 2(b).

Preferably, crystalline Form B is characterized by an infrared spectrum having bands at about 547, 661, 715, 781, 1065, 1196, 1296, 1514, 1656, and 3217 (cm$^{-1}$); more preferably, crystalline Form B is characterized by an infrared spectrum as depicted in FIG. 2(c).

In accordance with yet another embodiment, crystalline Form C of gemcitabine base is characterized by a powder x-ray diffraction pattern with peaks at about 15.6 and 22.3±0.2 degrees two-theta; preferably, crystalline Form C is further characterized by a powder x-ray diffraction pattern with peaks at about 14.4, 23.6, and 24.4±0.2 degrees two-theta; more preferably, crystalline Form C is further characterized by a powder x-ray diffraction pattern with peaks at about 12.1, 18.8, 23.0, 29.1, 34.5 and 34.8±0.2 degrees two-theta. As a preferred embodiment, crystalline Form C is characterized by a powder x-ray diffraction pattern as depicted in FIG. 3(a).

Preferably, crystalline Form C is characterized by a DSC thermogram having a sharp endothermic peak at about 221.61-223.73° C. More preferably, crystalline Form C is characterized by a DSC thermogram as depicted in FIG. 3(b).

Preferably, crystalline Form C is characterized by an infrared spectrum having bands at about 523, 781, 1086, 1199, 1297, 1492, 1656, and 3199 (cm$^{-1}$). More preferably, crystalline Form C is further characterized by an infrared spectrum as depicted in FIG. 3(c).

In accordance with yet another embodiment, crystalline Form D of gemcitabine base is characterized by a powder x-ray diffraction pattern with peaks at about 14.1 and 20.7±0.2 degrees two-theta; preferably, crystalline Form D is further characterized by a powder x-ray diffraction pattern with peaks at about 10.6, 14.9, 24.4, 27.8, and 30.3±0.2 degrees two-theta; more preferably, crystalline Form D is further characterized by a powder x-ray diffraction pattern with peaks at about 10.1, 17.3, 19.0, 19.7, 22.2, 23.0, 12.1, 18.8, 23.0, and 32.2±0.2 degrees two-theta. As a preferred embodiment, crystalline Form D is characterized by a powder x-ray diffraction pattern as depicted in FIG. 4(a).

Preferably, crystalline Form D is characterized by a DSC thermogram as depicted in FIG. 4(b).

Preferably, crystalline Form D is further characterized by an infrared spectrum having bands at about 598, 784, 1097, 1523, 1654, and 3407 (cm$^{-1}$). More preferably, crystalline Form D is characterized by an infrared spectrum as depicted in FIG. 4(c).

In accordance with yet another embodiment, crystalline Form E of gemcitabine base is characterized by a powder x-ray diffraction pattern with peaks at about 20.8 and 23.5±0.2 degrees two-theta; preferably, crystalline Form E is further characterized by a powder x-ray diffraction pattern with peaks at about 10.3, 11.8, 27.5, and 30.0±0.2 degrees two-theta; more preferably, crystalline Form E is further characterized by a powder x-ray diffraction pattern with peaks at about 10.5, 15.8, 22.0, 23.0, 24.7, 28.1, and 33.0±0.2 degrees two-theta. As a preferred embodiment, crystalline Form E is further characterized by a powder x-ray diffraction pattern as depicted in FIG. 5(a).

Preferably, the crystalline Form E is further characterized as depicted in FIG. 5(b).

Preferably, crystalline Form E is characterized by an infrared spectrum having bands at about 577, 782, 1096, 1523, 1662, and 3406 ($cm^{-1}$). More preferably, crystalline Form E is characterized by an infrared spectrum as depicted in FIG. 5(c).

In accordance with yet another embodiment, crystalline Form F of gemcitabine base is characterized by a powder x-ray diffraction pattern with peaks at about 20.8 and 27.6±0.2 degrees two-theta; preferably, crystalline Form F is characterized by a powder x-ray diffraction pattern with peaks at about 9.4, 11.8, 15.8, 24.3, and 30.1±0.2 degrees two-theta; more preferably, crystalline Form F is further characterized by a powder x-ray diffraction pattern with peaks at about 16.1, 16.8, 22.0, 28.2, and 33.0±0.2 degrees two-theta. As a preferred embodiment, crystalline Form F is characterized by a powder x-ray diffraction pattern as depicted in FIG. 6(a).

Preferably, crystalline Form F is characterized by a DSC thermogram as depicted in FIG. 6(b).

Preferably, crystalline Form F is characterized by an infrared spectrum having bands at about 781, 1059, 1094, 1523, 1660, and 3404 ($cm^{-1}$). More preferably, Form F is characterized by an infrared spectrum as depicted in FIG. 6(c).

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

DETAILED DESCRIPTION OF THE PRESENTLY PREFERRED EMBODIMENTS

Figure 1A:
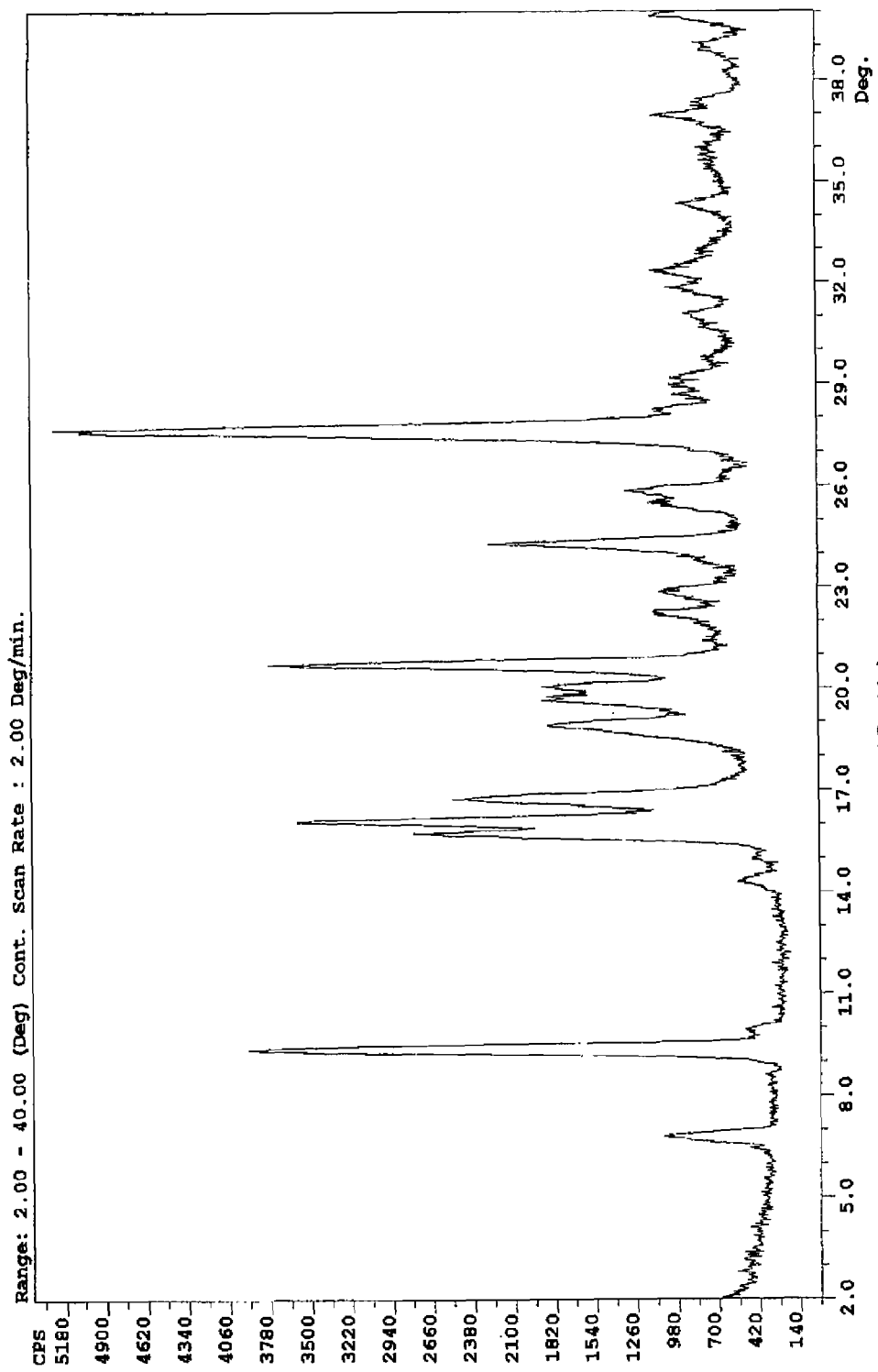
FIG. 1 is the X-ray powder diffraction pattern (a), the DSC pattern (b), and the Infrared spectrum (c) for crystalline Form A of gemcitabine base.
Figure 1A:
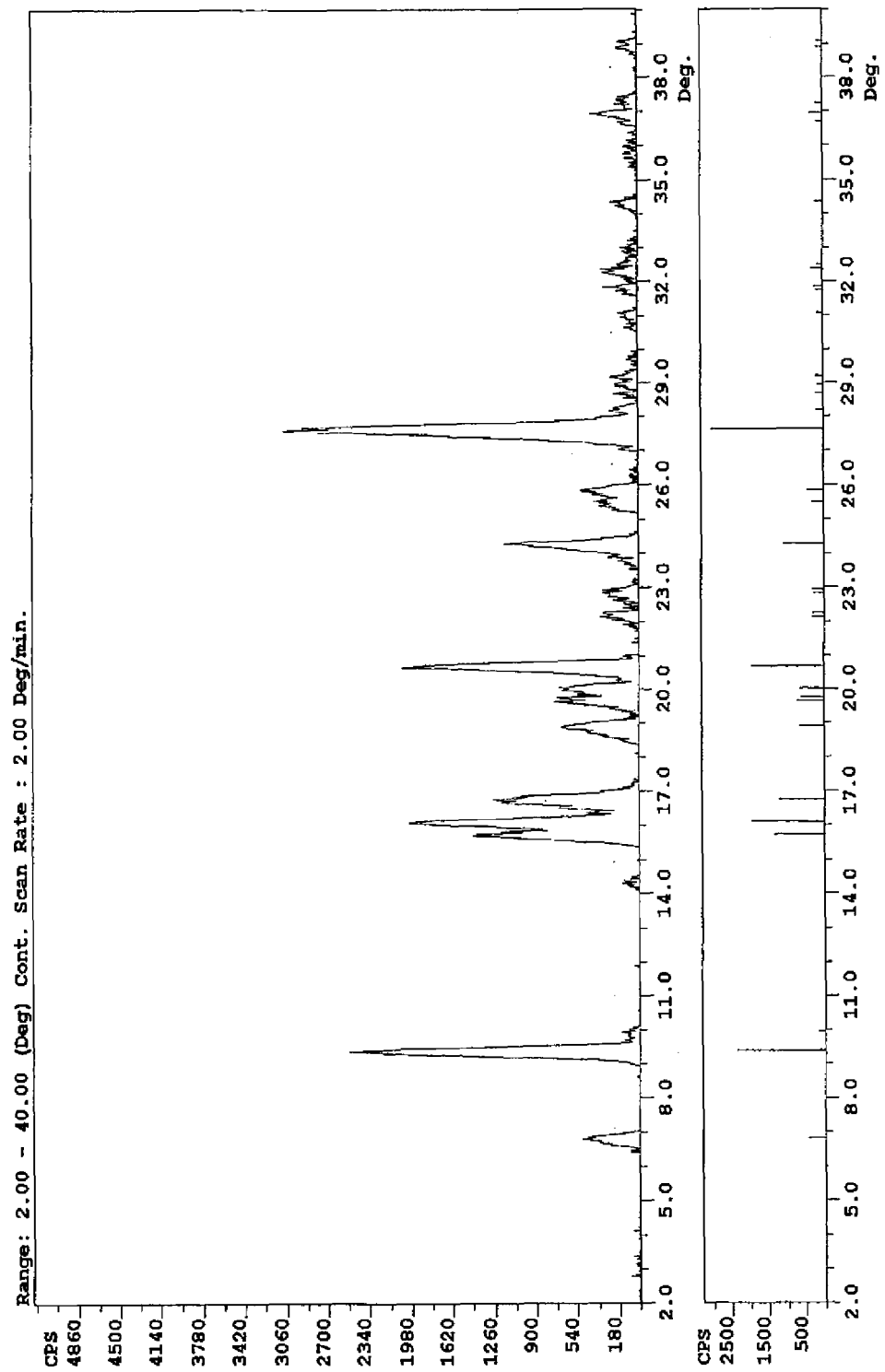
Figure 1B:
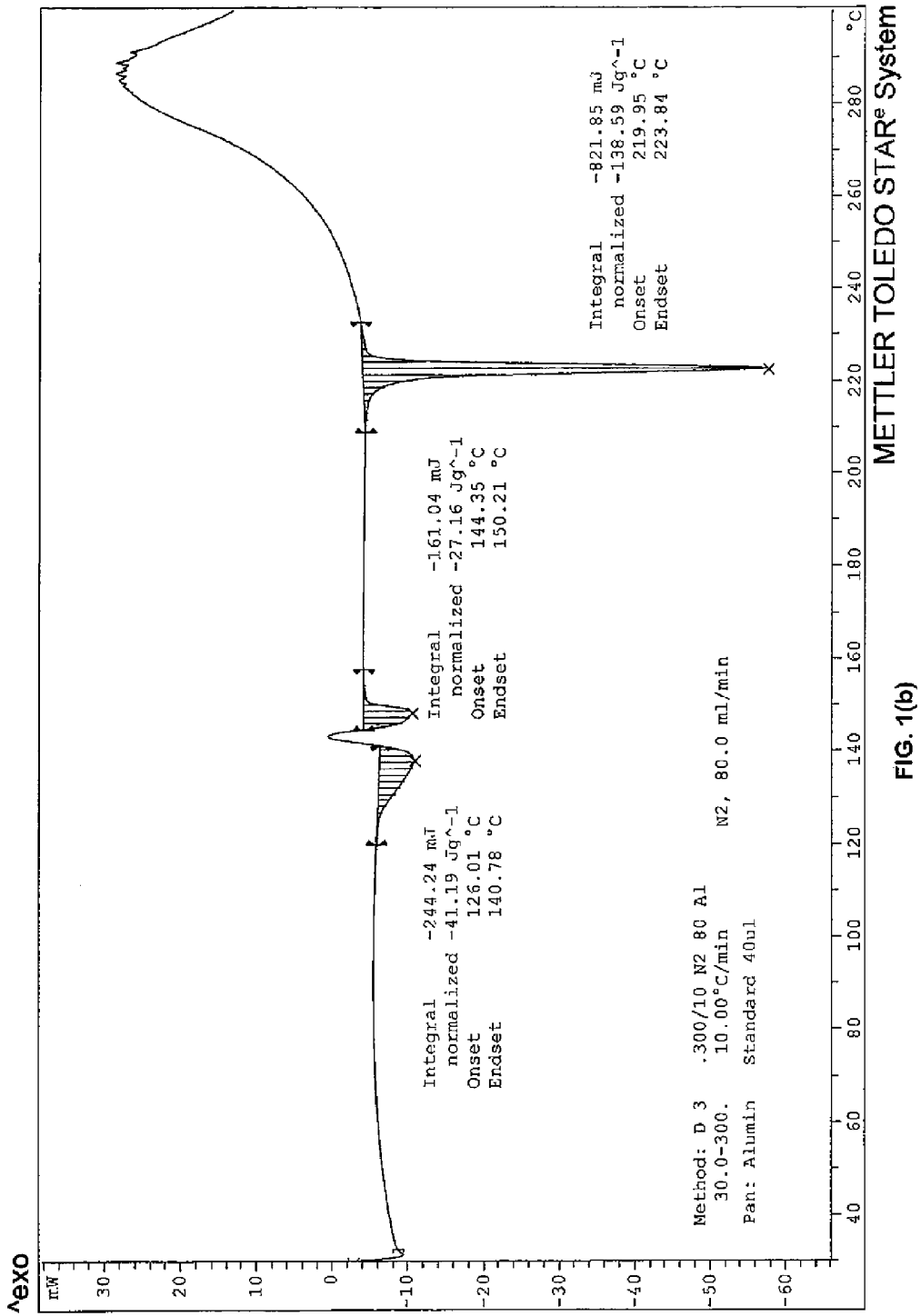
Figure 1C:
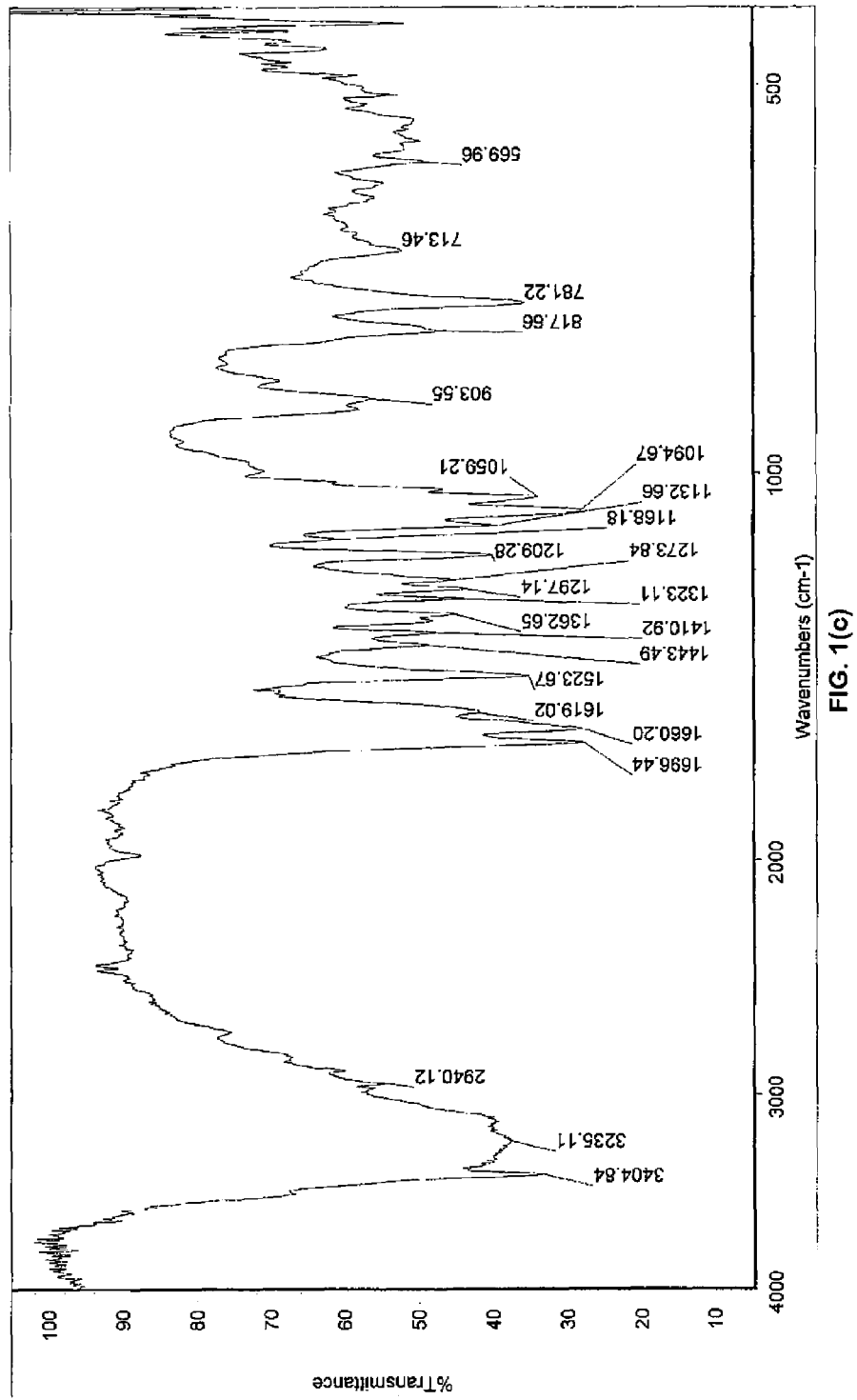
Figure 1C:
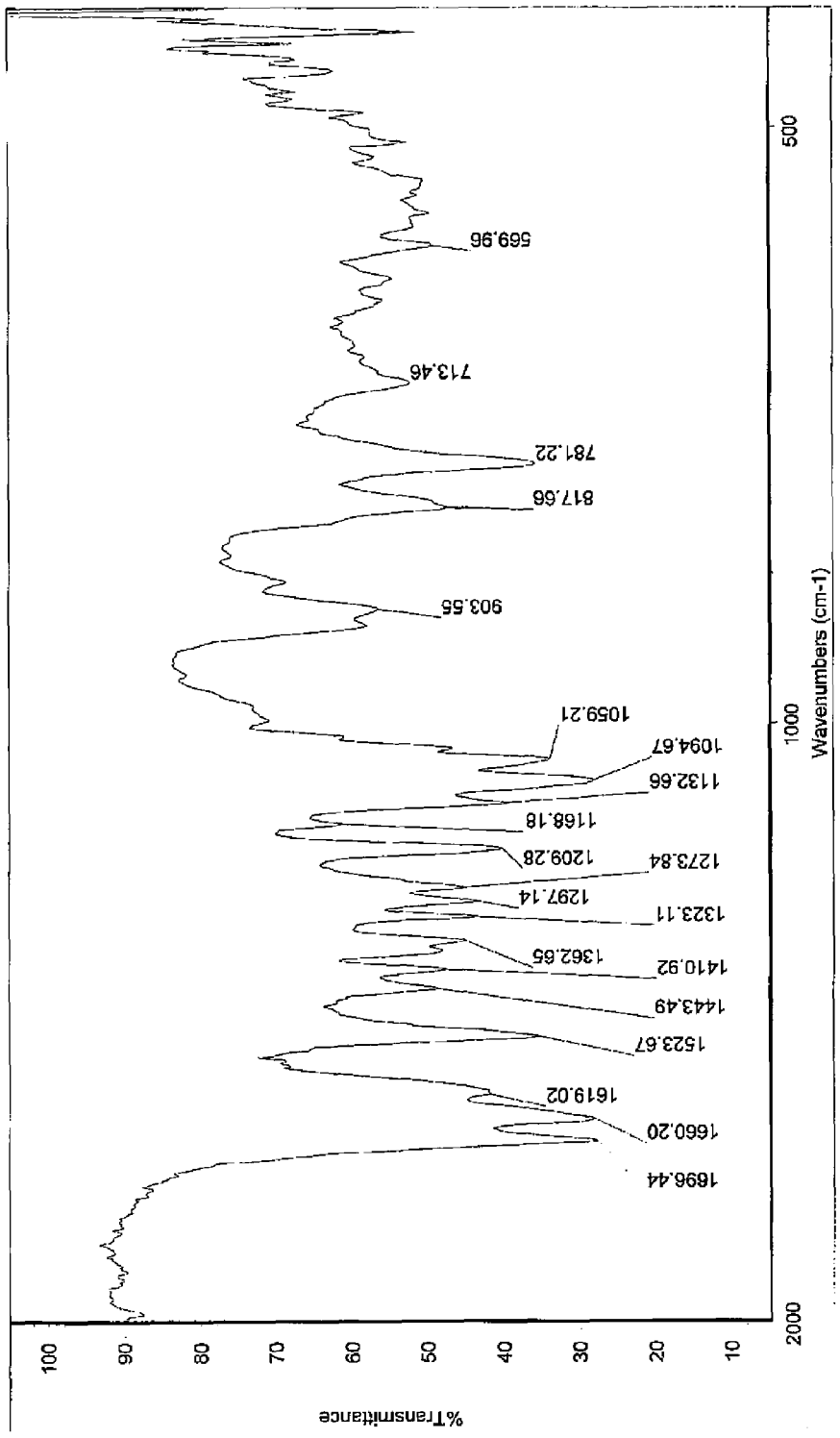

The following examples are provided to illustrate, but not to limit the present invention.

EXAMPLES

Example 1

1 g Gemcitabine is dissolved in 5 mL MeOH at RT (20-30° C.). 10 mL toluene is added to reaction mixture and solid begins to precipitate out. The reaction mixture is cooled to 0-10° C. and filtered. The solid is Gemcitabine Form A.

Example 2

1 g Gemcitabine is dissolved in 5 mL MeOH at RT (20-30° C.). 10 mL EA is added to reaction mixture and solid begins to precipitate out. The reaction mixture is cooled to 0-10° C. and filtered. The solid is Gemcitabine Form A.

Example 3

1 g Gemcitabine is dissolved in 5 mL water and 5 mL EtOH at 40° C. 10 mL MTBE is added to reaction mixture and solid begins to precipitate out. The reaction mixture is cooled to 0-10° C. and filtered. The solid is Gemcitabine Form B.

Example 4

1 g Gemcitabine is dissolved in 5 mL MeOH at RT (20-30° C.). 10 mL $CH_2Cl_2$ is added to reaction mixture and solid begins to precipitate out. The reaction mixture is cooled to 0-10° C. and filtered. The solid is Gemcitabine Form A.

Example 5

1 g Gemcitabine is dissolved in 10 mL EtOH at reflux temp. The reaction mixture is cooled to 0-10° C. and filtered. The solid is Gemcitabine Form A.

Example 6

1 g Gemcitabine is dissolved in 18 mL MeOH and 1 mL water at 70° C. 54 mL EA is added to reaction mixture and solid begins to precipitate out. The reaction mixture is cooled to 0-10° C. and filtered. The solid is Gemcitabine Form A.

Example 7

1 g Gemcitabine is dissolved in 5 mL MeOH and 25 mL ACN at RT (20-30° C.). 25 mL n-heptane° is added to reaction mixture and solid begins to precipitate out. The reaction mixture is cooled to 0-10° C. and filtered. The solid is Gemcitabine Form A.

Example 8

1 g Gemcitabine is dissolved in 30 mL acetone. 30 mL $CH_2Cl_2$ is added to the reaction mixture and solid begins to precipitate out. The reaction mixture is cooled to 0-10° C. and filtered. The solid is Gemcitabine Form E.

Example 9

1 g Gemcitabine is dissolved in 30 mL THF and 30 mL water at 50-60° C. The reaction mixture is cooled to 0-10° C. and filtered. The solid is Gemcitabine Form B.

Example 10

1 g Gemcitabine is dissolved in 2 mL water and 36 mL IPA at 70° C. The reaction mixture is cooled to 0-10° C. and filtered. The solid is Gemcitabine Form A.

Example 11

1 g Gemcitabine is dissolved in 6 mL water and 60 mL ACN at 70° C. The reaction mixture is cooled to 0-10° C. and filtered. The solid is Gemcitabine Form F.

Example 12

1 g Gemcitabine is dissolved in 16 mL water 50-60° C. The reaction mixture is cooled to 0-10° C. and filtered. The solid is Gemcitabine Form B.

Example 13

1 g Gemcitabine is dissolved in 5 mL MeOH at RT (20-30° C.). 15 mL MIBK is added to reaction mixture and solid begins to precipitate out. The reaction mixture is cooled to 0-10° C. and filtered. The solid is Gemcitabine Form A.

Example 14

1 g Gemcitabine is dissolved in 2 mL water and 20 mL n-butanol at 70° C. The reaction mixture is cooled to 0-10° C. and filtered. The solid is Gemcitabine Form A.

Example 15

1 g Gemcitabine is dissolved in 2 mL water and 20 mL IPA at 70° C. The reaction mixture is cooled to 0-10° C. and filtered. The solid is Gemcitabine Form B.

Example 16

1 g Gemcitabine is dissolved in water/IPA=95/5, 90/10, at 70° C. The reaction mixture is cooled to 0-10° C. and filtered and Gemcitabine dried for 2 hours at 60° C. under vacuum, to obtain Gemcitabine Form D.

Example 17

1 g Gemcitabine is dissolved in water/IPA=95/5 or 90/10 at 70° C. The reaction mixture is cooled to 0-10° C. and filtered. The solid is Gemcitabine form B. After 2 hours of drying at 60° C. under vacuum, Gemcitabine Form B is converted to Form A.

Example 18

1 g Gemcitabine is dissolved in water/IPA=85/15, at 70° C. The reaction mixture is cooled to 0-10° C. and filtered. The solid is Gemcitabine form A+B. After 2 hours of drying at 60° C. under vacuum, Gemcitabine Form B is converted to Form A.

Example 19

Form C is an anhydrous form from heating Form A at 200° C.

Table 1 blow summarizes production of various crystalline forms of gemcitabine in accordance with the embodiments provided above.

TABLE 1

| Item | Solvent system (part by Volume) | Crystal form |
|---|---|---|
| 1 | MeOH/Toluene = 5/10 | A |
| 2 | MeOH/EA = 5/10 | A |
| 3 | $H_2O$/EtOH/MTBE = 5/5/10 | B |
| 4 | MeOH/$CH_2Cl_2$ = 5/10 | A |
| 5 | EtOH = 10 | A |
| 6 | IPA/$H_2O$/EA = 18/1/54 | A |
| 7 | MeOH/ACN/n-hep = 5/20/10 | A |
| 8 | Acetone/$CH_2Cl_2$ = 30/30 | E |
| 9 | THF/$H_2O$ = 30/30 | B |
| 10 | IPA/$H_2O$ = 36/2 | A |
| 11 | AcN/$H_2O$ = 60/6 | F |
| 12 | $H_2O$ | B |
| 13 | MeOH/MIBK = 5/15 | A |
| 14 | n-butanol/water = 20/2 | A |
| 15 | IPA/$H_2O$ = 20/2 | B |
| 16 | IPA/$H_2O$ = 5/95, 10/90 | D |
| 17 | $H_2O$/EtOH/MTBE = 5/5/10 | B |
| 18 | IPA/H2O = 36/2 | A |

Table 2 below shows the solubility of Form A in different solvents.

| solvent | MeOH | EtOH | IPA | Butanol | Acetone | MIBK | MTBE | THF | Toluene |
|---|---|---|---|---|---|---|---|---|---|
| Solubility (mg/mL) | 201.16 | 26.23 | 8.36 | 4.92 | 5.9 | 0.054 | 0 | 0.84 | 0 |
| solvent | $H_2O$ | ACN | EA | n-heptane | $CH_2Cl_2$ | DMAC | DMSO | | |
| Solubility (mg/mL) | 20.32 | 1.78 | 0.06 | 0 | 0 | >468.06 | 217.22 | | |

The invention is not limited by the embodiments described above which are presented as examples only but can be modified in various ways within the scope of protection defined by the appended patent claims.

We claim:

1. Crystalline Form A of gemcitabine base characterized by a powder x-ray diffraction pattern with peaks at about 27.6 and 9.4±0.2 degrees two-theta.

2. The crystalline Form A of claim 1 further characterized by a powder x-ray diffraction pattern with peaks at about 16.1 and 20.7±0.2 degrees two-theta.

3. The crystalline Form A of claim 1 further characterized by a powder x-ray diffraction pattern with peaks at about 6.8, 15.7, 16.7, and 24.3±0.2 degrees two-theta.

4. The crystalline Form A of claim 1 further characterized by a powder x-ray diffraction pattern as depicted in FIG. 1(*a*).

5. Crystalline Form B of gemcitabine base characterized by a powder x-ray diffraction pattern with peaks at about 20.8 and 23.5±0.2 degrees two-theta.

6. The crystalline Form B of claim 5 further characterized by a powder x-ray diffraction pattern with peaks at about 11.8, 27.8, and 30.1±0.2 degrees two-theta.

7. The crystalline Form B of claim 5 further characterized by a powder x-ray diffraction pattern with peaks at about 10.5, 15.8, 22.0, and 33.0±0.2 degrees two-theta.

Figure 2A:
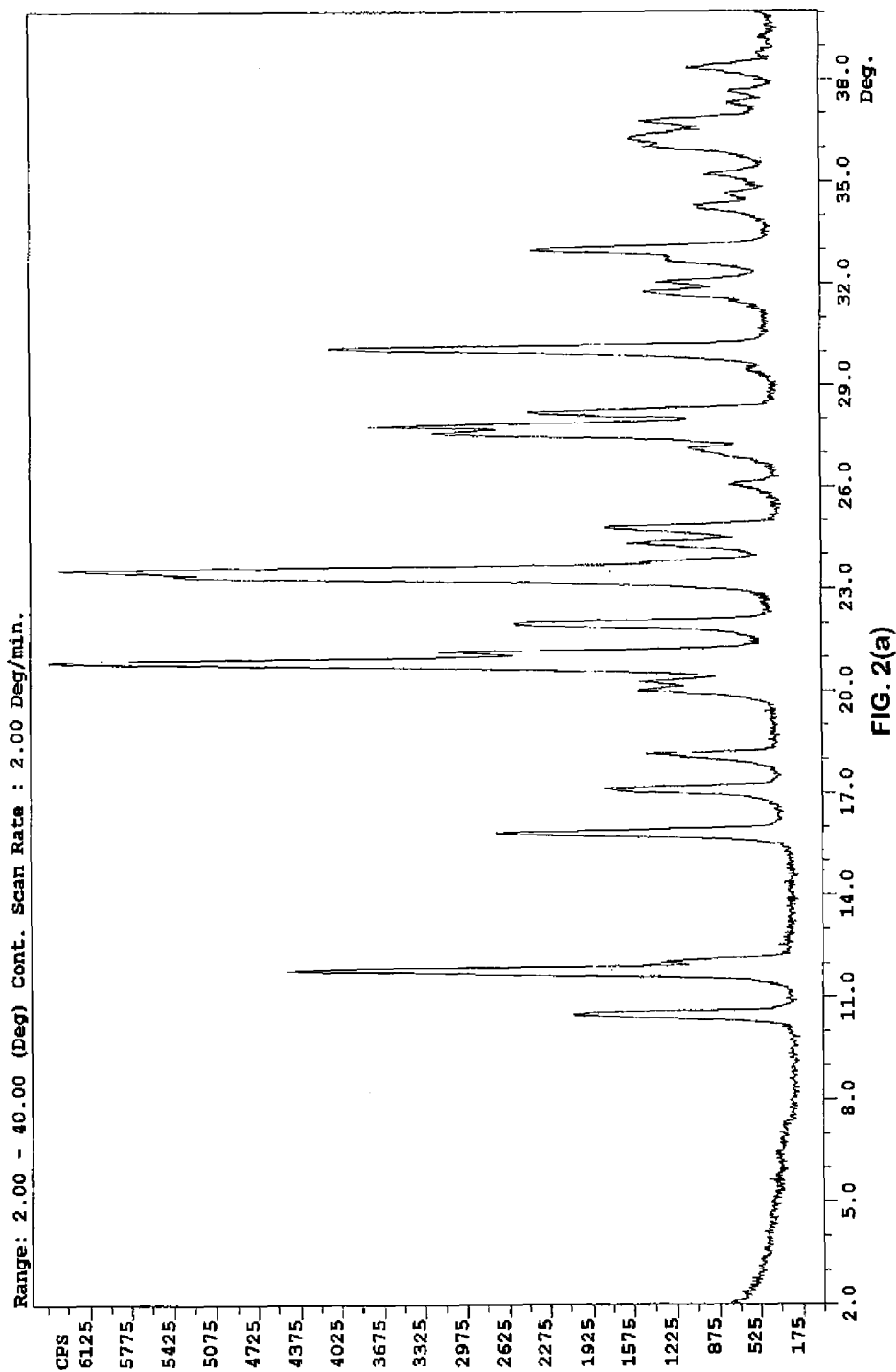
FIG. 2 is the X-ray powder diffraction pattern (a), the DSC pattern (b), and the Infrared spectrum (c) for crystalline Form B of gemcitabine base.
Figure 2A:
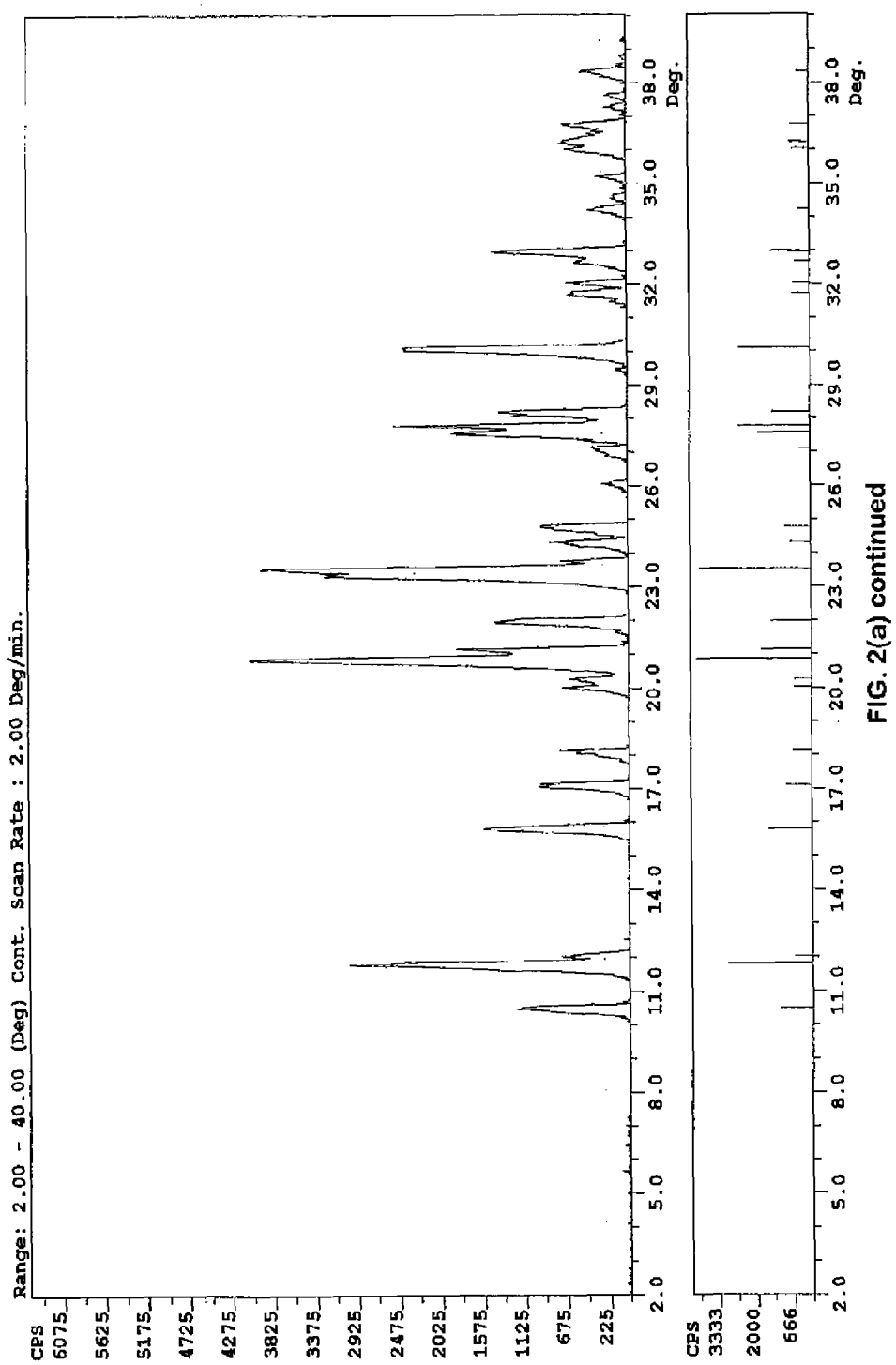
Figure 2B:
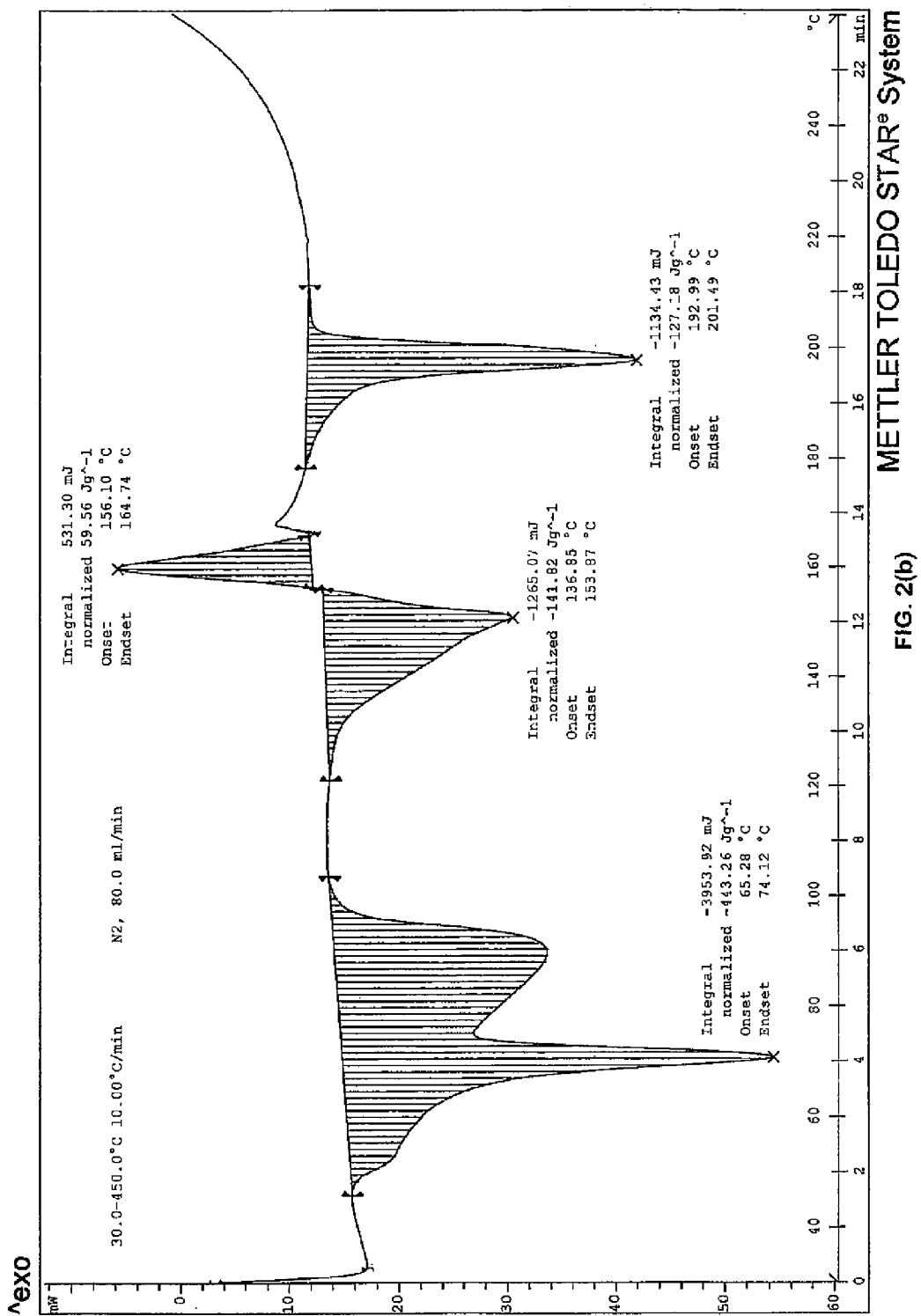
Figure 2C:
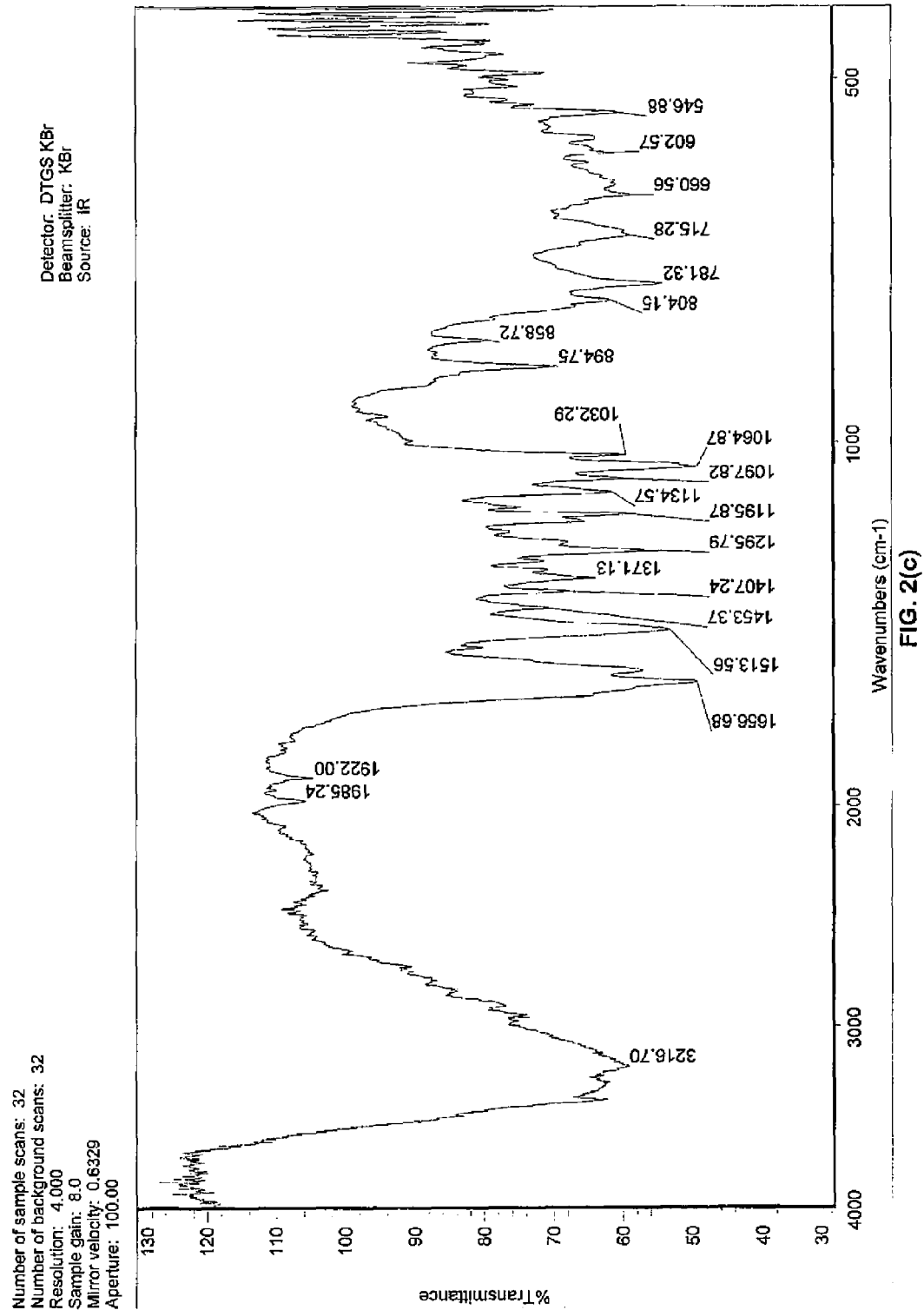
Figure 2C:
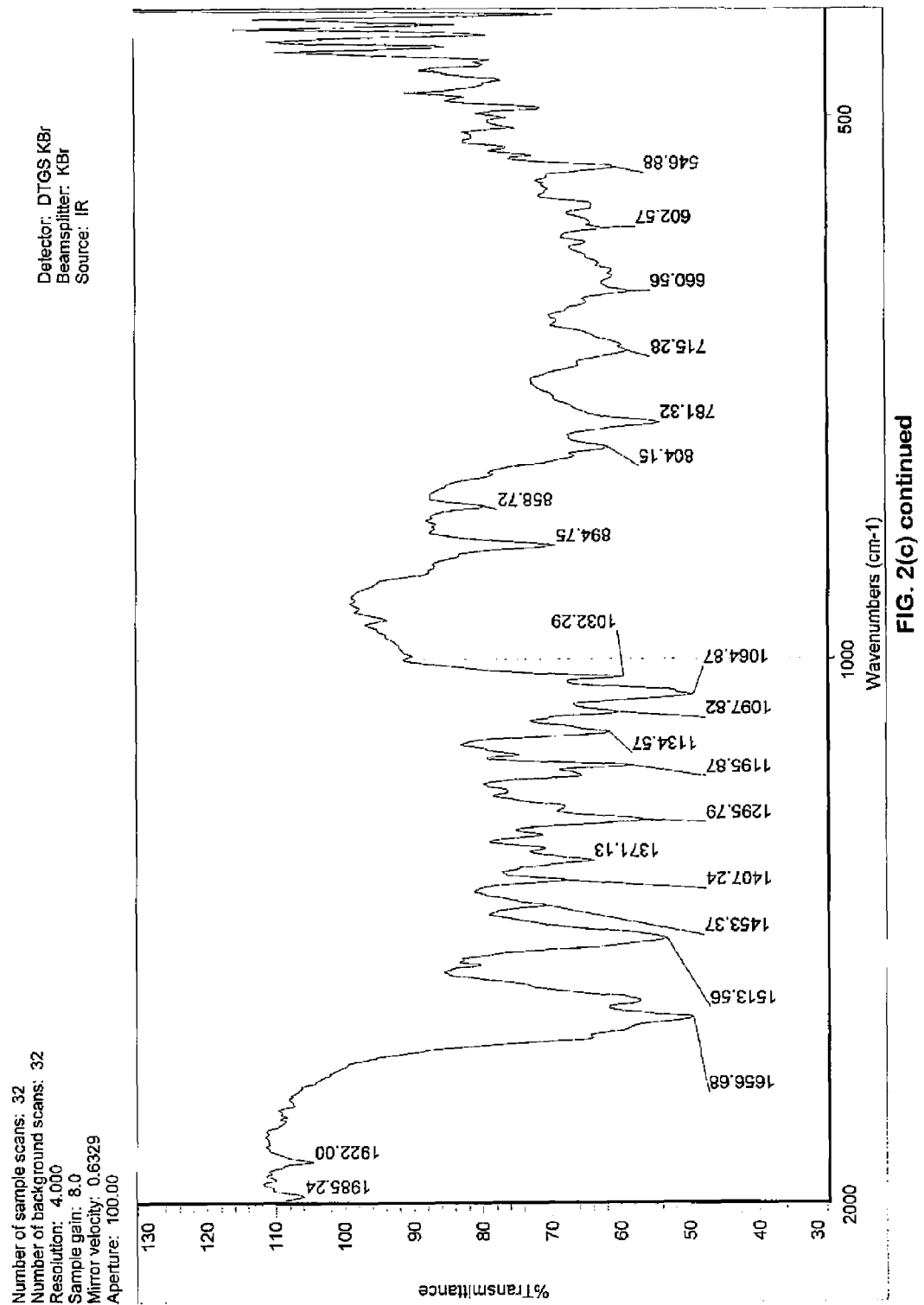

8. The crystalline Form B of claim 5 further characterized by a powder x-ray diffraction pattern as depicted in FIG. 2(a).

9. Crystalline Form C of gemcitabine base characterized by a powder x-ray diffraction pattern with peaks at about 15.6 and 22.3±0.2 degrees two-theta.

10. The crystalline Form C of claim 9 further characterized by a powder x-ray diffraction pattern with peaks at about 14.4, 23.6, and 24.4±0.2 degrees two-theta.

11. The crystalline Form C of claim 9 further characterized by a powder x-ray diffraction pattern with peaks at about 12.1, 18.8, 23.0, 29.1, 34.5 and 34.8±0.2 degrees two-theta.

Figure 3A:
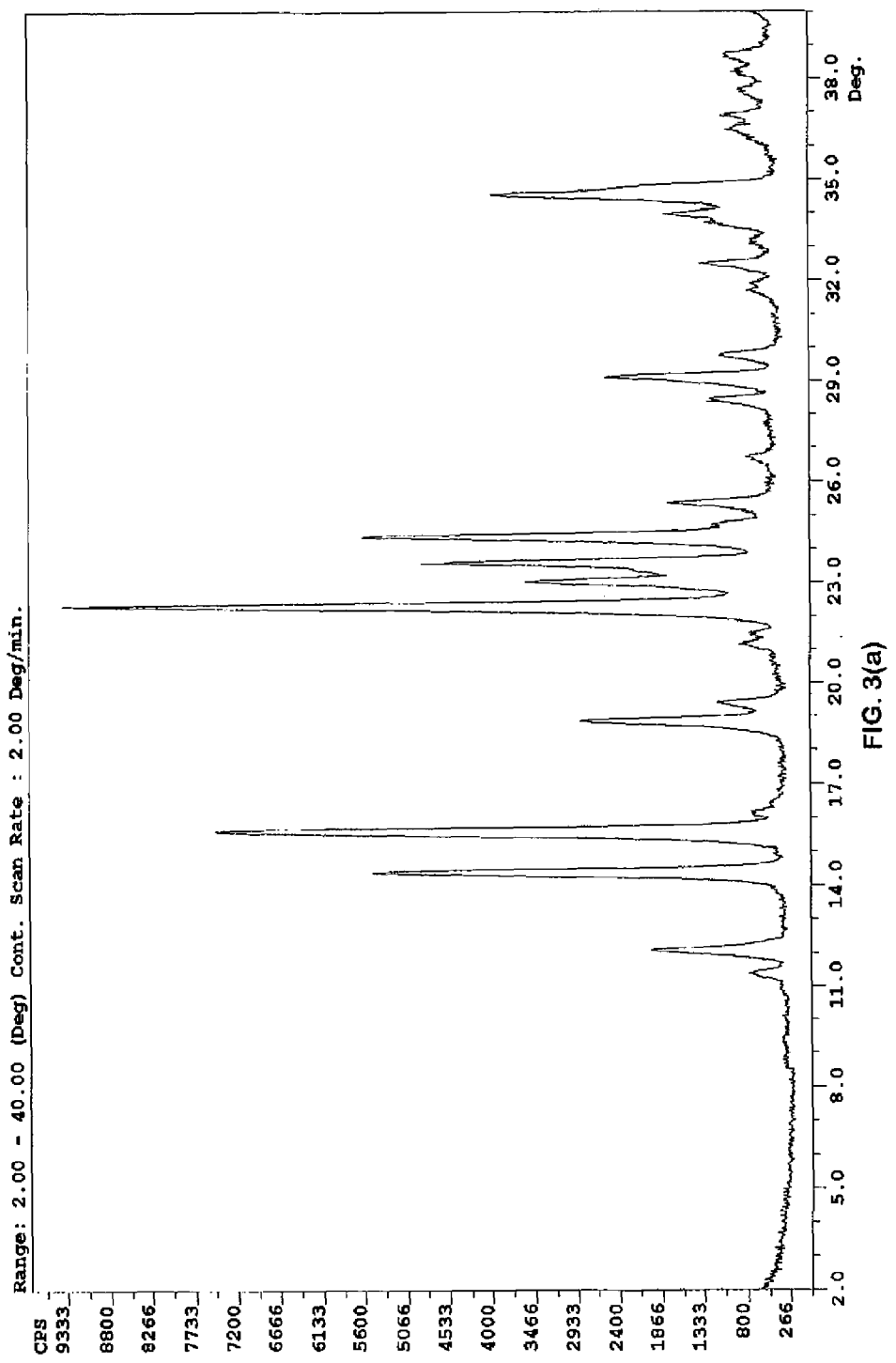
FIG. 3 is the X-ray powder diffraction pattern (a), the DSC pattern (b), and the Infrared spectrum (c) for crystalline Form C of gemcitabine base.
Figure 3A:
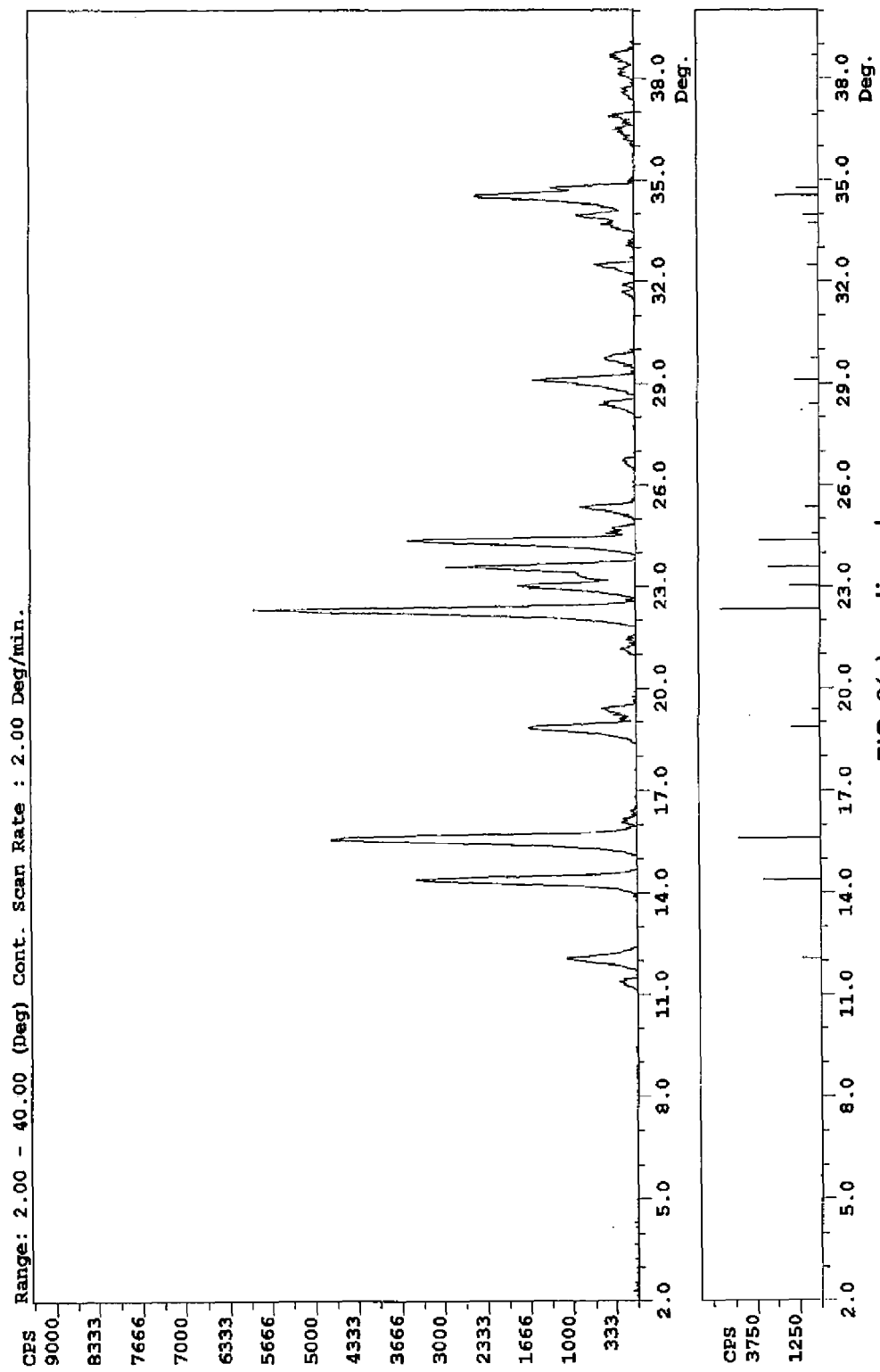
Figure 3B:
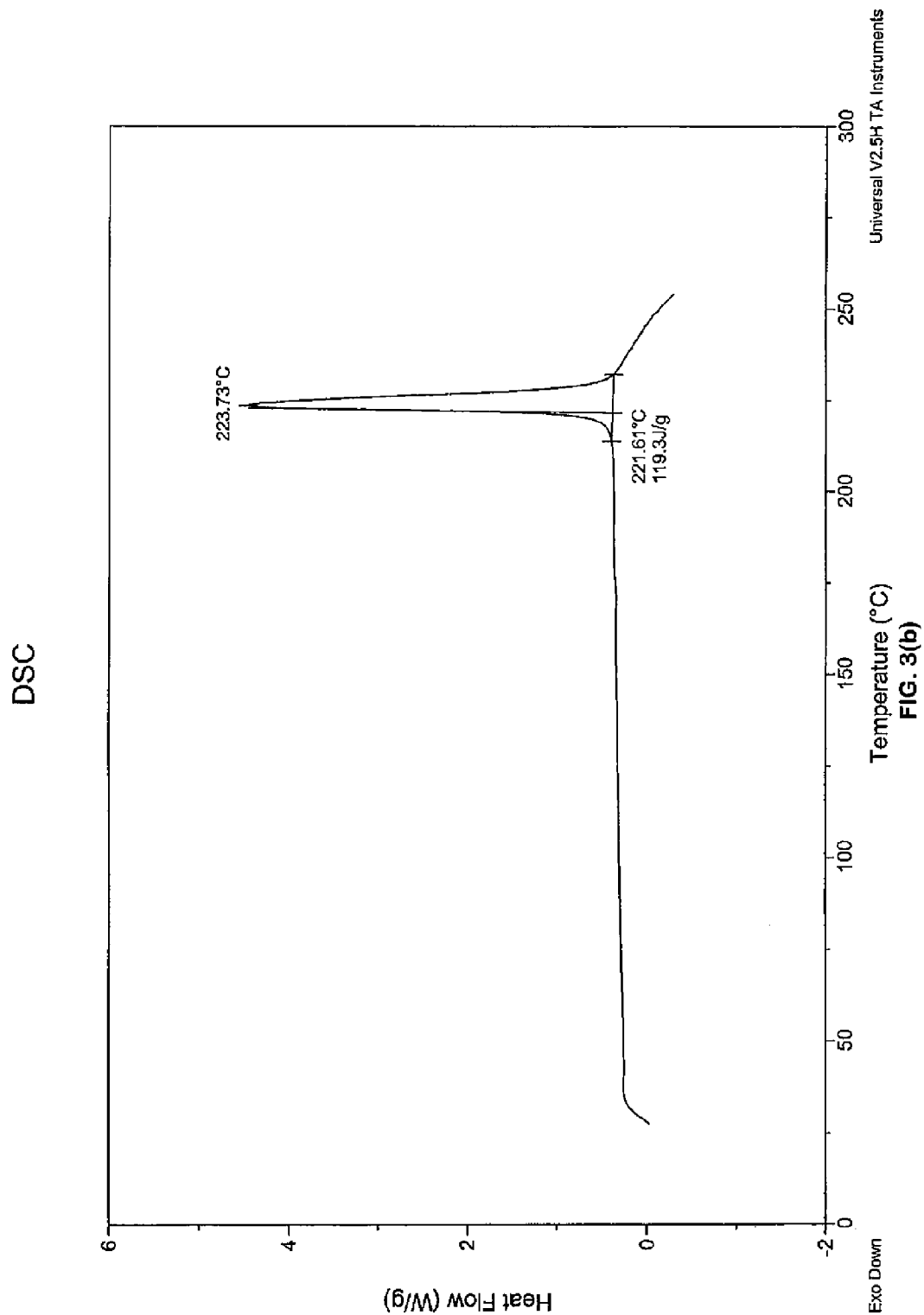
Figure 3C:
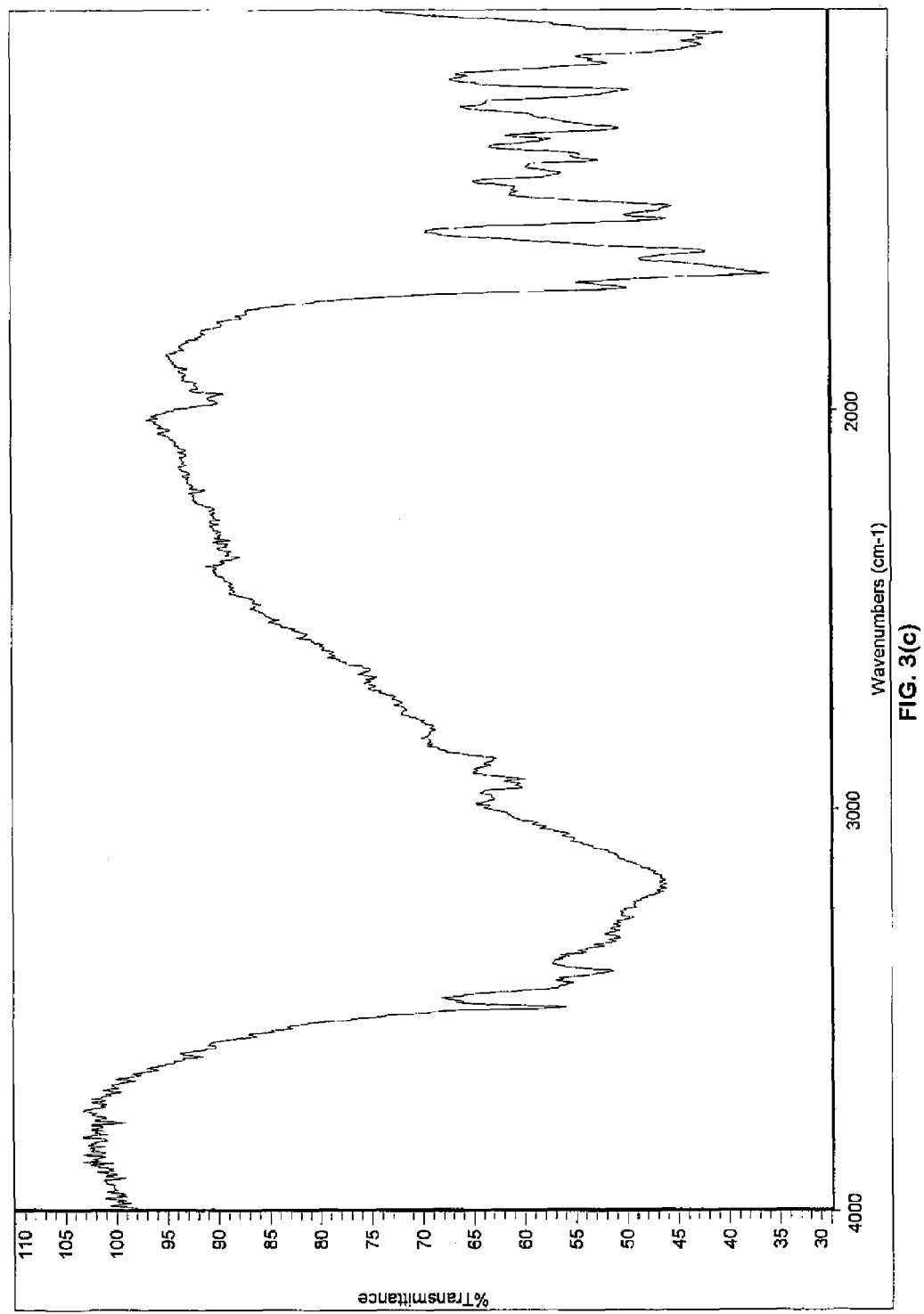
Figure 3C:
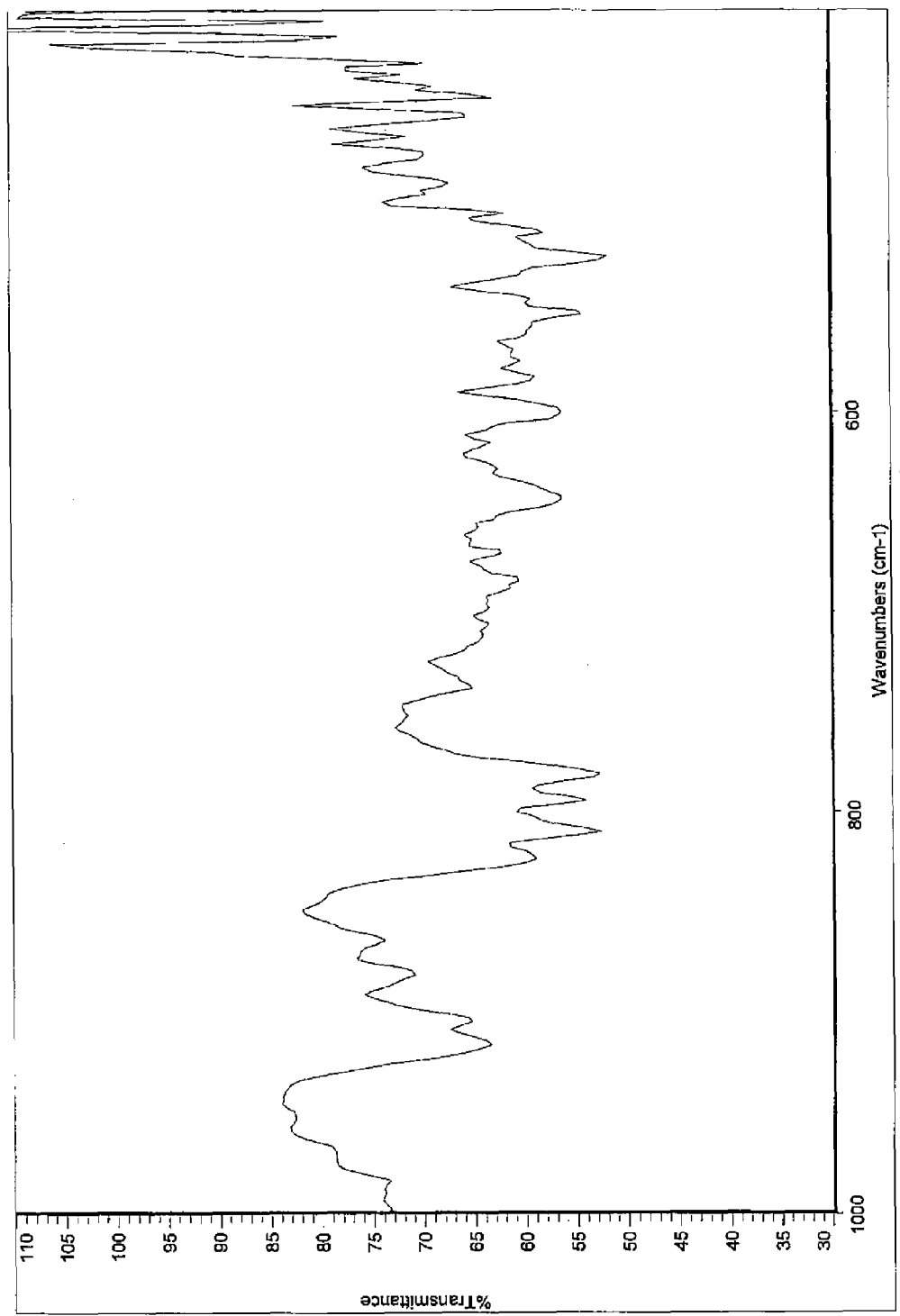

12. The crystalline Form C of claim 9 further characterized by a powder x-ray diffraction pattern as depicted in FIG. 3(a).

13. Crystalline Form D of gemcitabine base characterized by a powder x-ray diffraction pattern with peaks at about 14.1 and 20.7±0.2 degrees two-theta.

14. The crystalline Form D of claim 13 further characterized by a powder x-ray diffraction pattern with peaks at about 10.6, 14.9, 24.4, 27.8, and 30.3±0.2 degrees two-theta.

15. The crystalline Form D of claim 13 further characterized by a powder x-ray diffraction pattern with peaks at about 10.1, 17.3, 19.0, 19.7, 22.2, 23.0, 12.1, 18.8, 23.0, and 32.2±0.2 degrees two-theta.

Figure 4A:
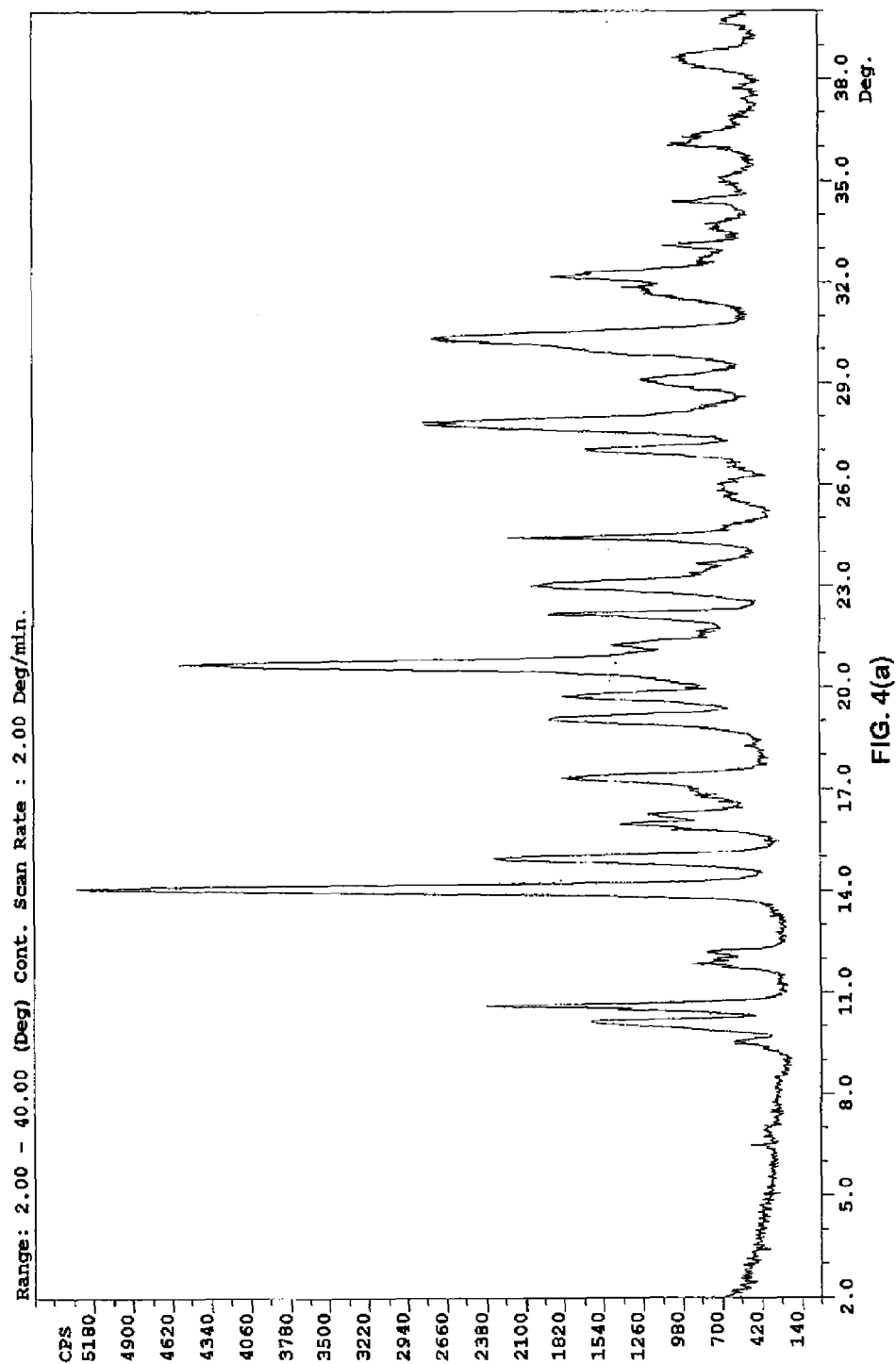
FIG. 4 is the X-ray powder diffraction pattern (a), the DSC pattern (b), and the Infrared spectrum (c) for crystalline Form D of gemcitabine base.
Figure 4A:
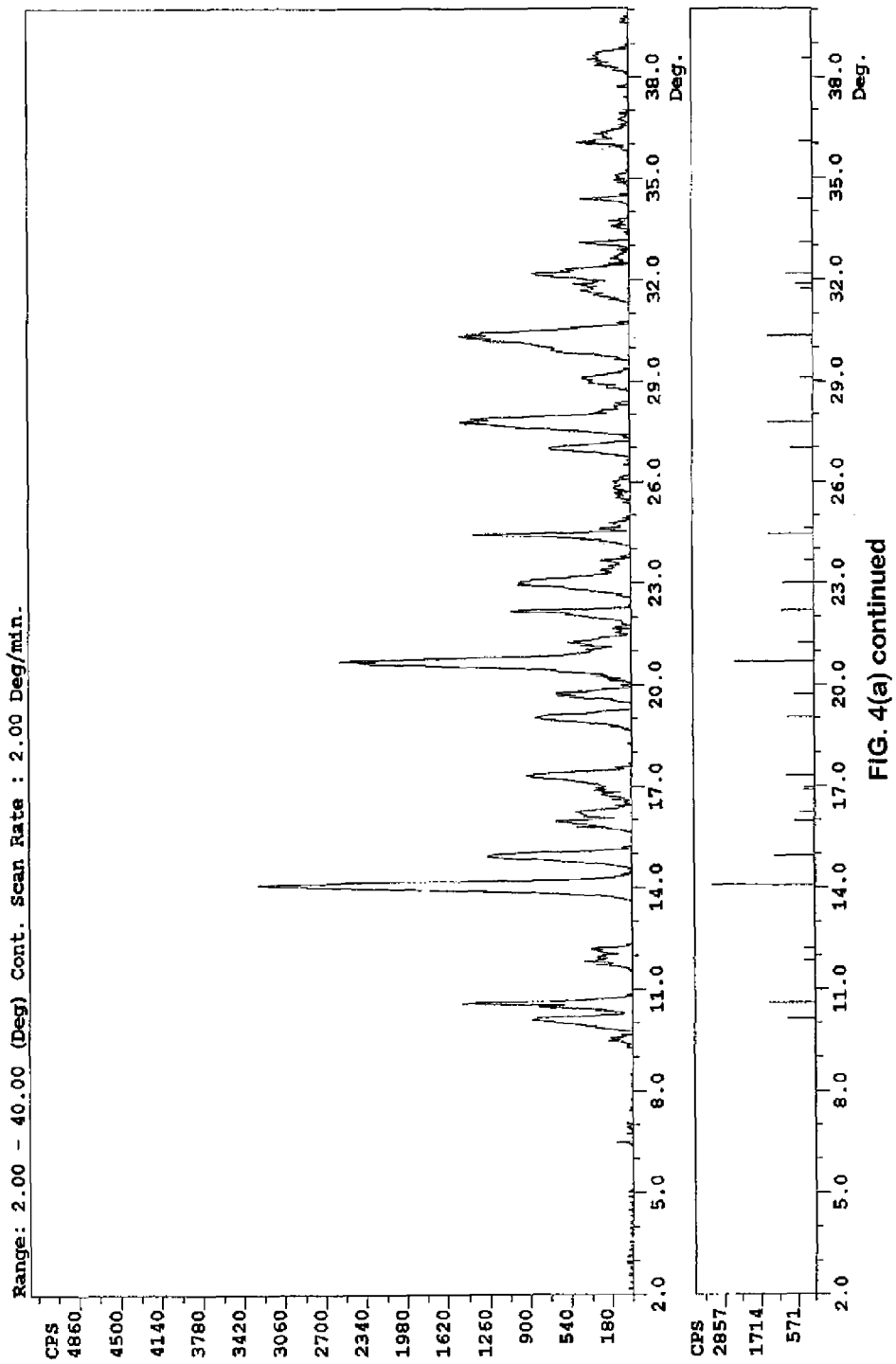
Figure 4B:
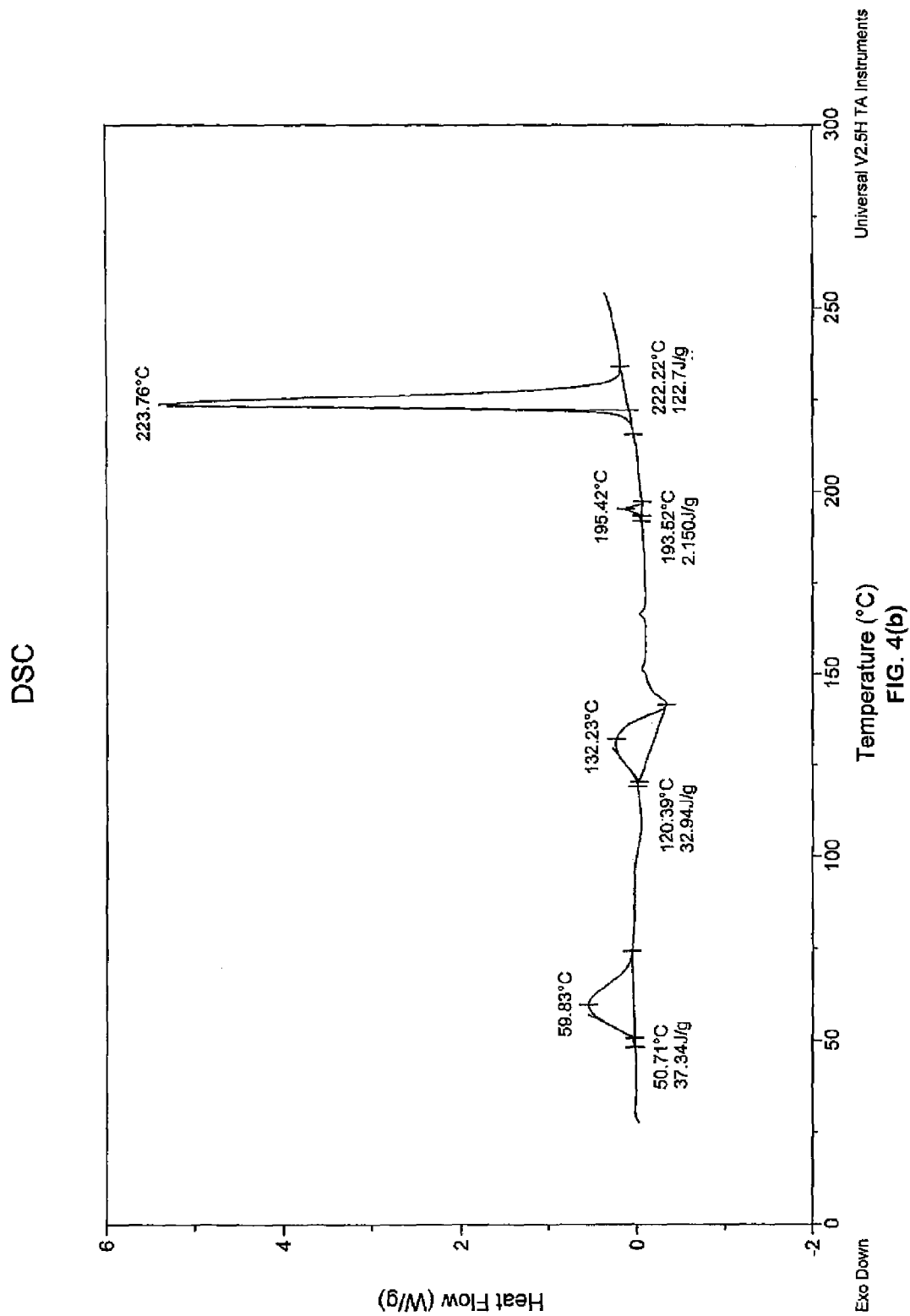
Figure 4C:
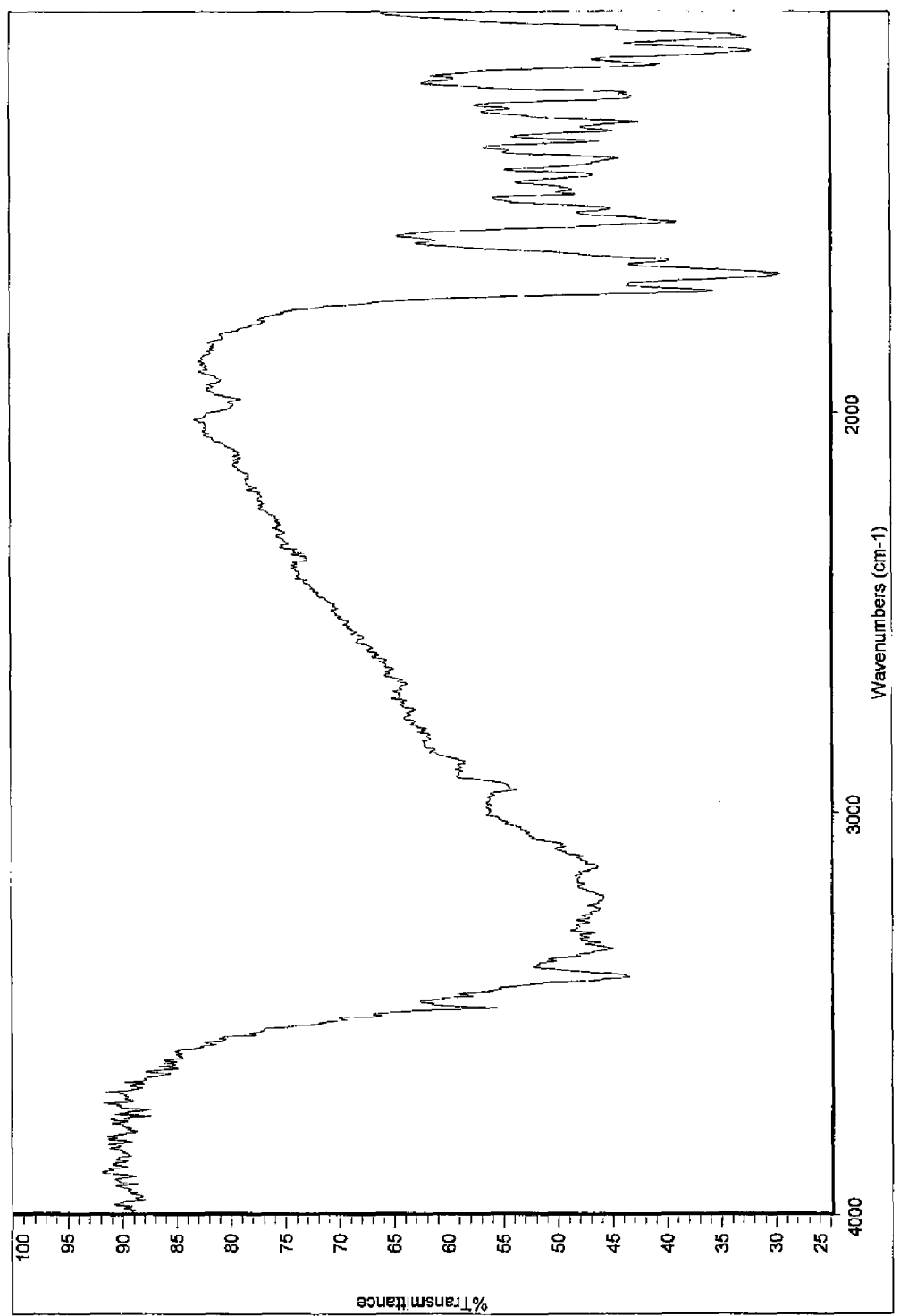
Figure 4C:
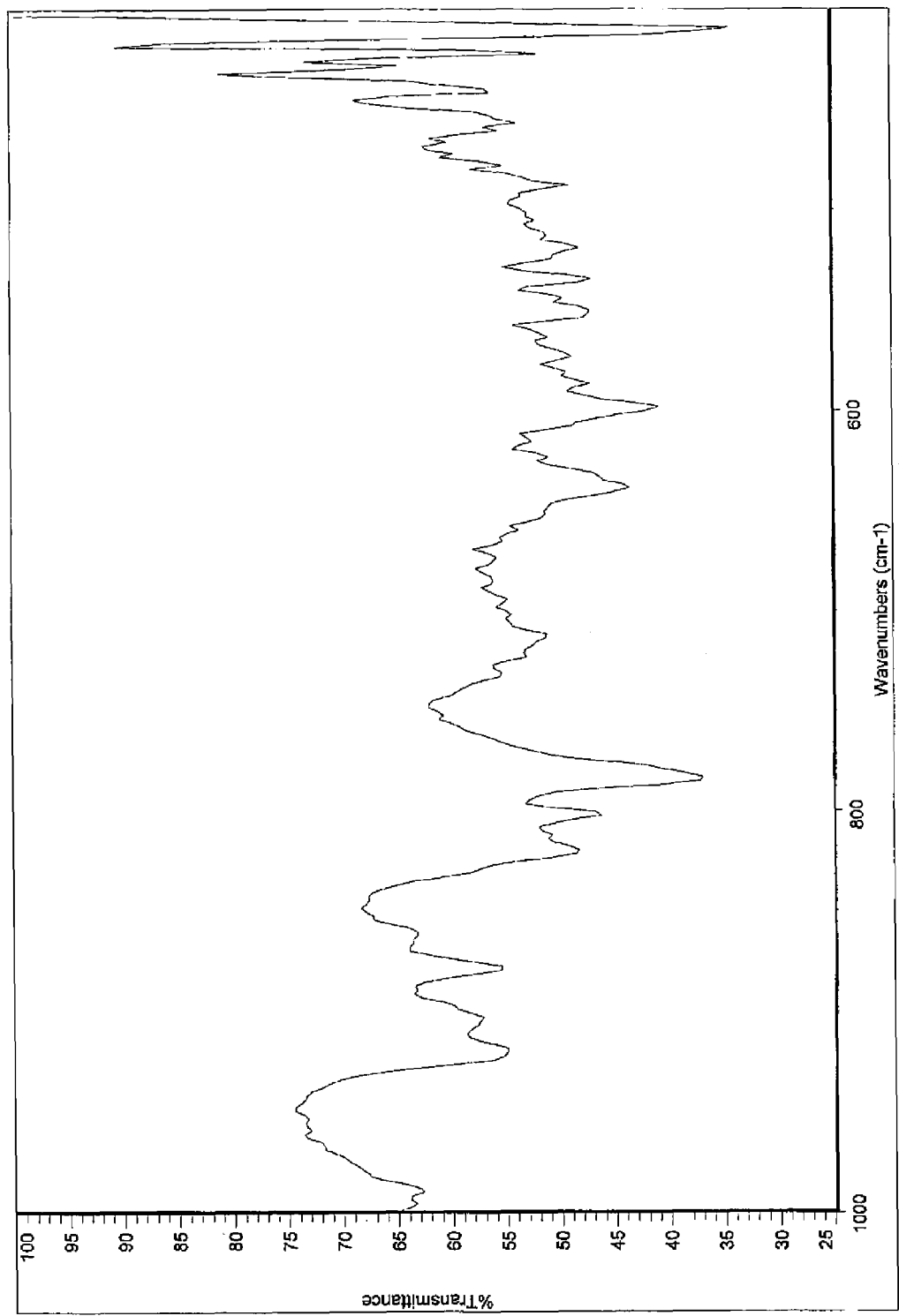

16. The crystalline Form D of claim 13 further characterized by a powder x-ray diffraction pattern as depicted in FIG. 4(a).

17. Crystalline Form E of gemcitabine base characterized by a powder x-ray diffraction pattern with peaks at about 20.8 and 23.5±0.2 degrees two-theta.

18. The crystalline Form E of claim 17 further characterized by a powder x-ray diffraction pattern with peaks at about 10.3, 11.8, 27.5, and 30.0±0.2 degrees two-theta.

19. The crystalline Form E of claim 17 further characterized by a powder x-ray diffraction pattern with peaks at about 10.5, 15.8, 22.0, 23.0, 24.7, 28.1, and 33.0±0.2 degrees two-theta.

Figure 5A:
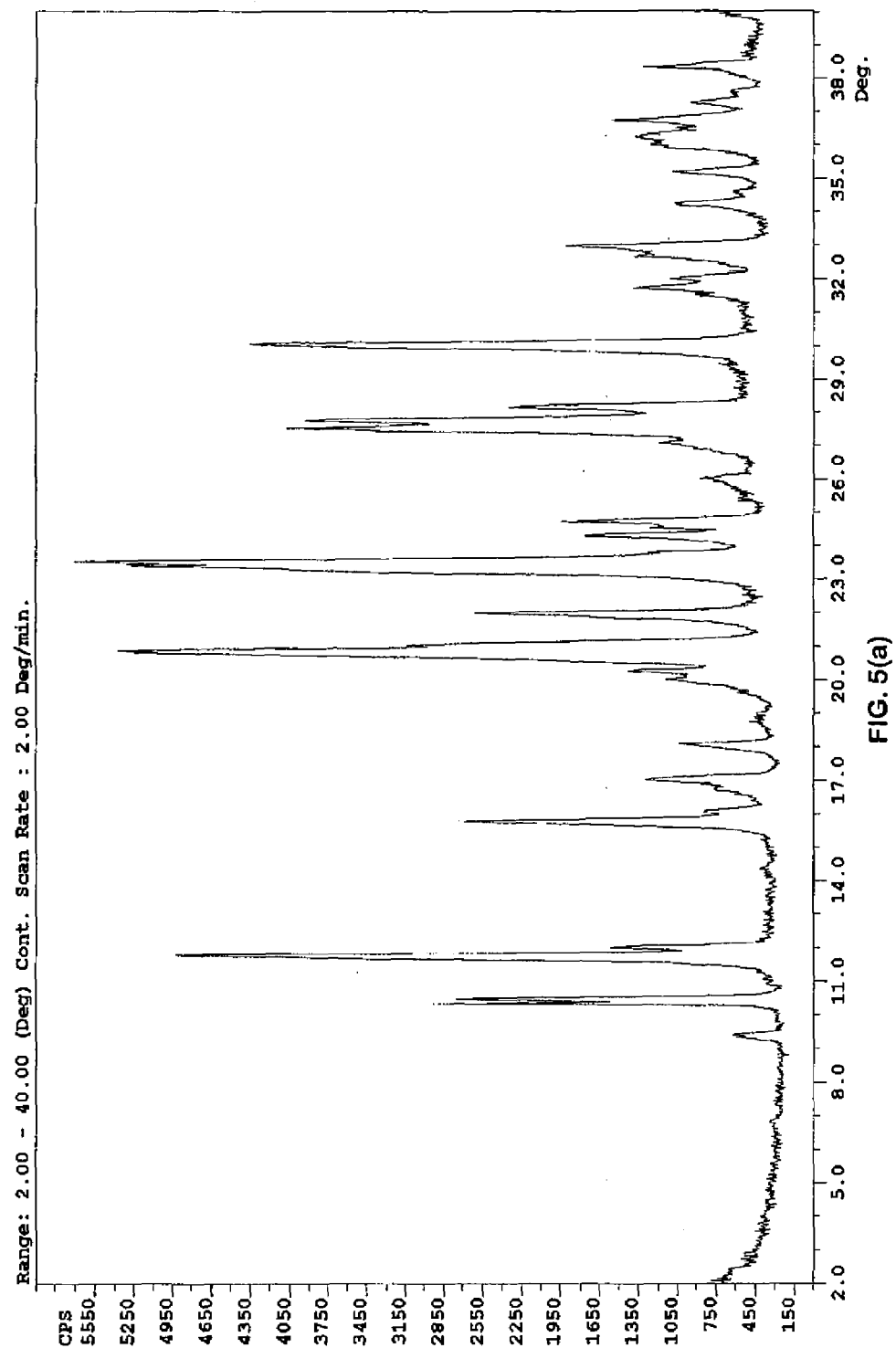
FIG. 5 is the X-ray powder diffraction pattern (a), the DSC pattern (b), and the Infrared spectrum (c) for crystalline Form E of gemcitabine base.
Figure 5A:
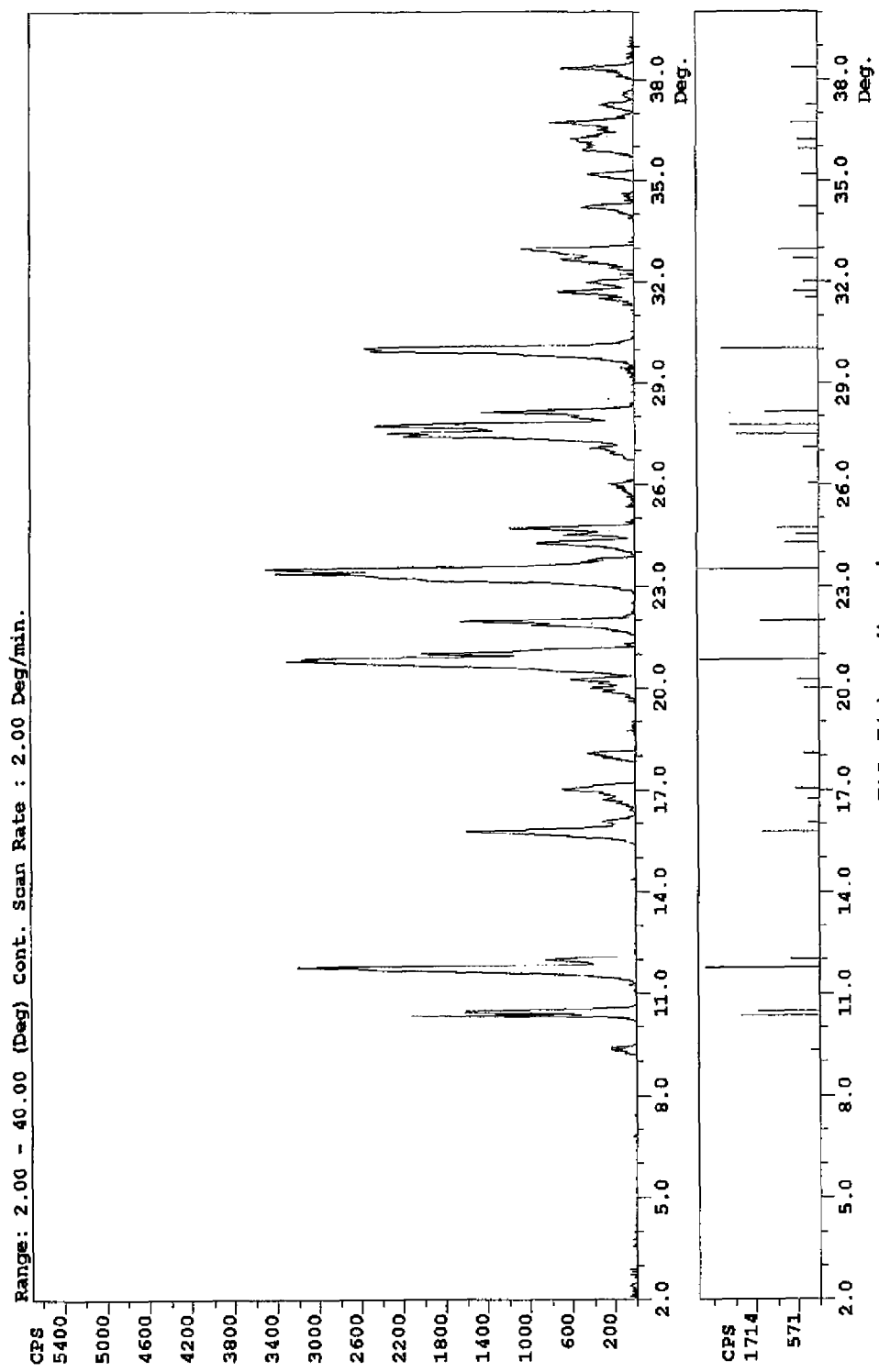
Figure 5B:
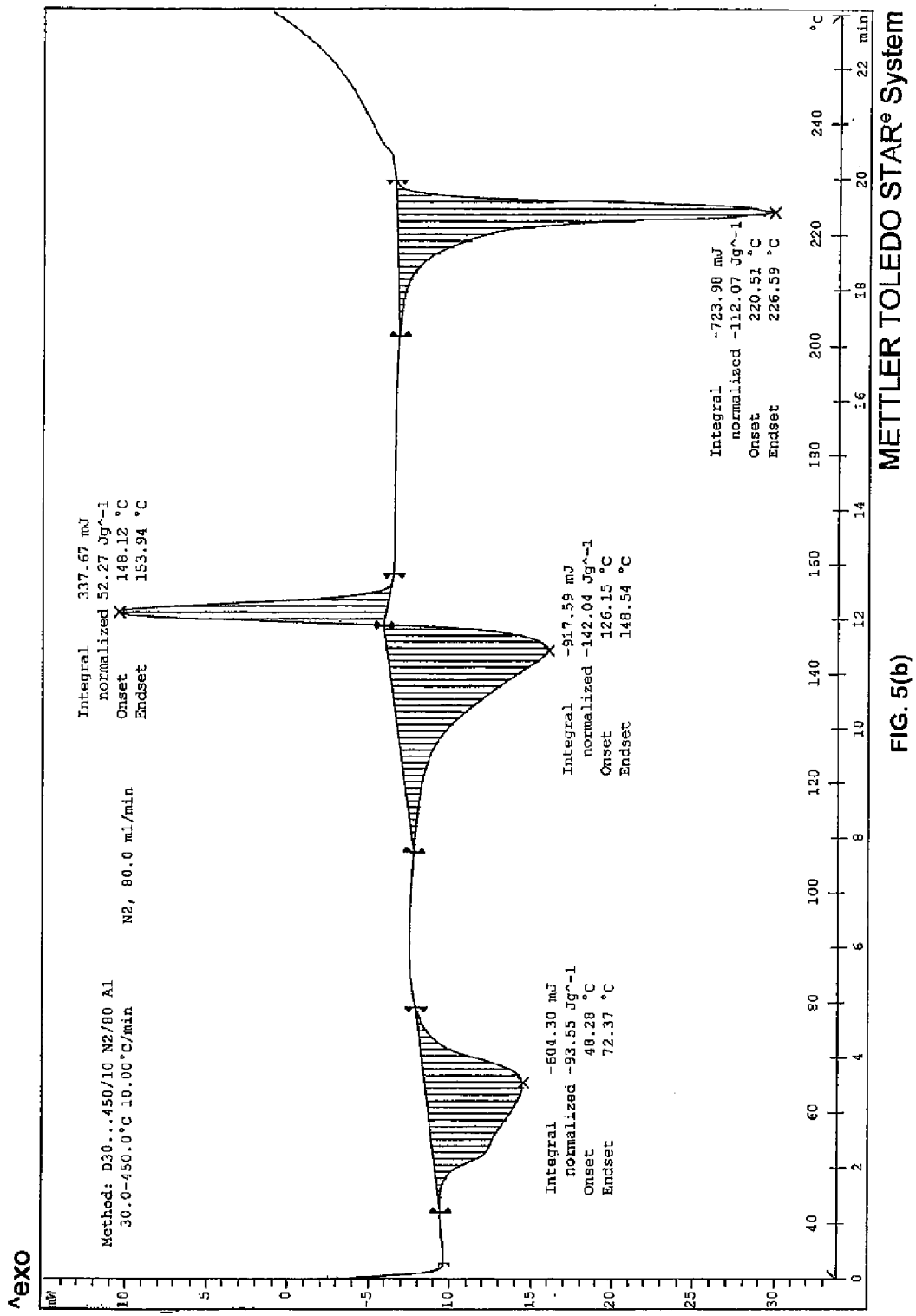
Figure 5C:
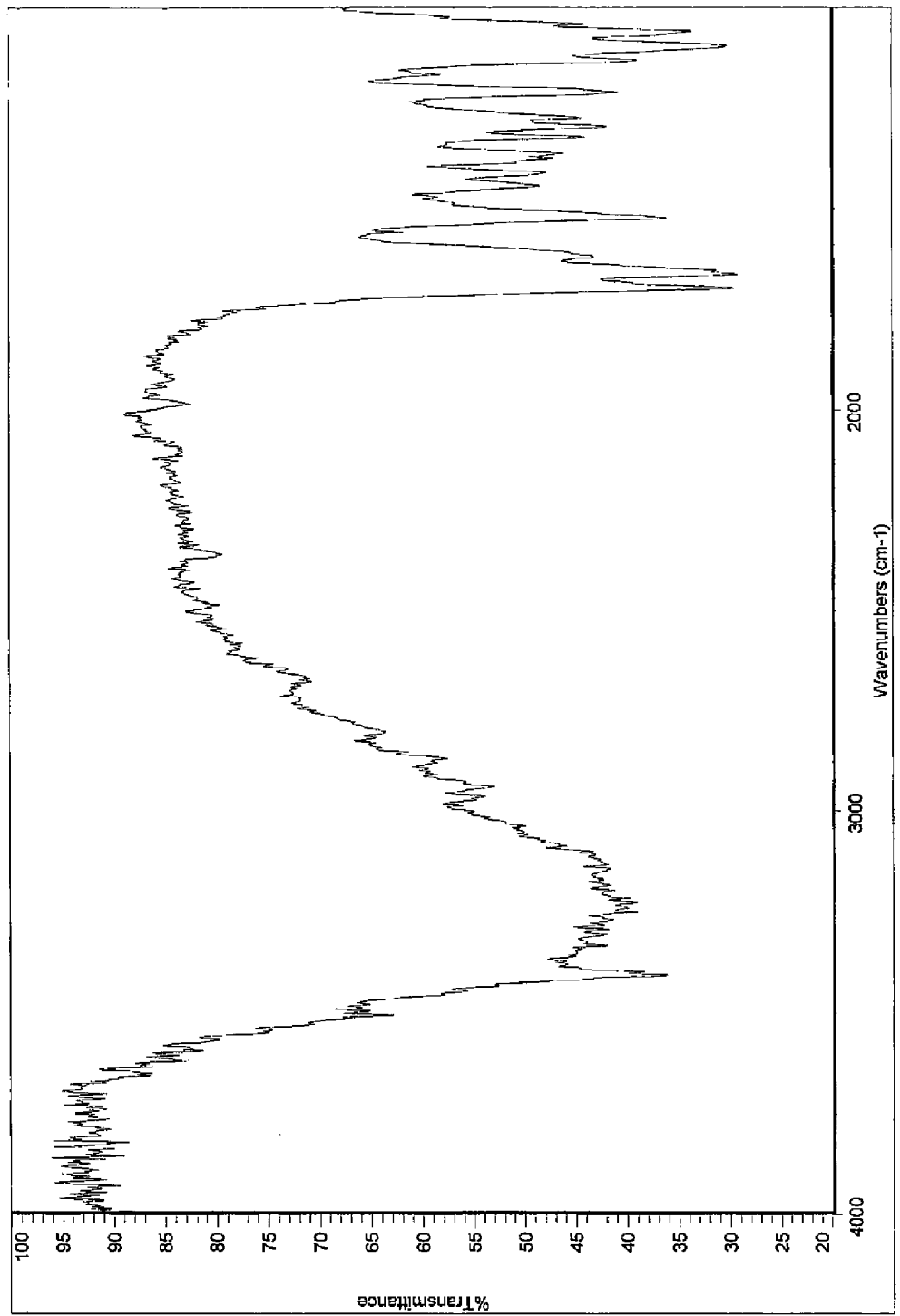
Figure 5C:
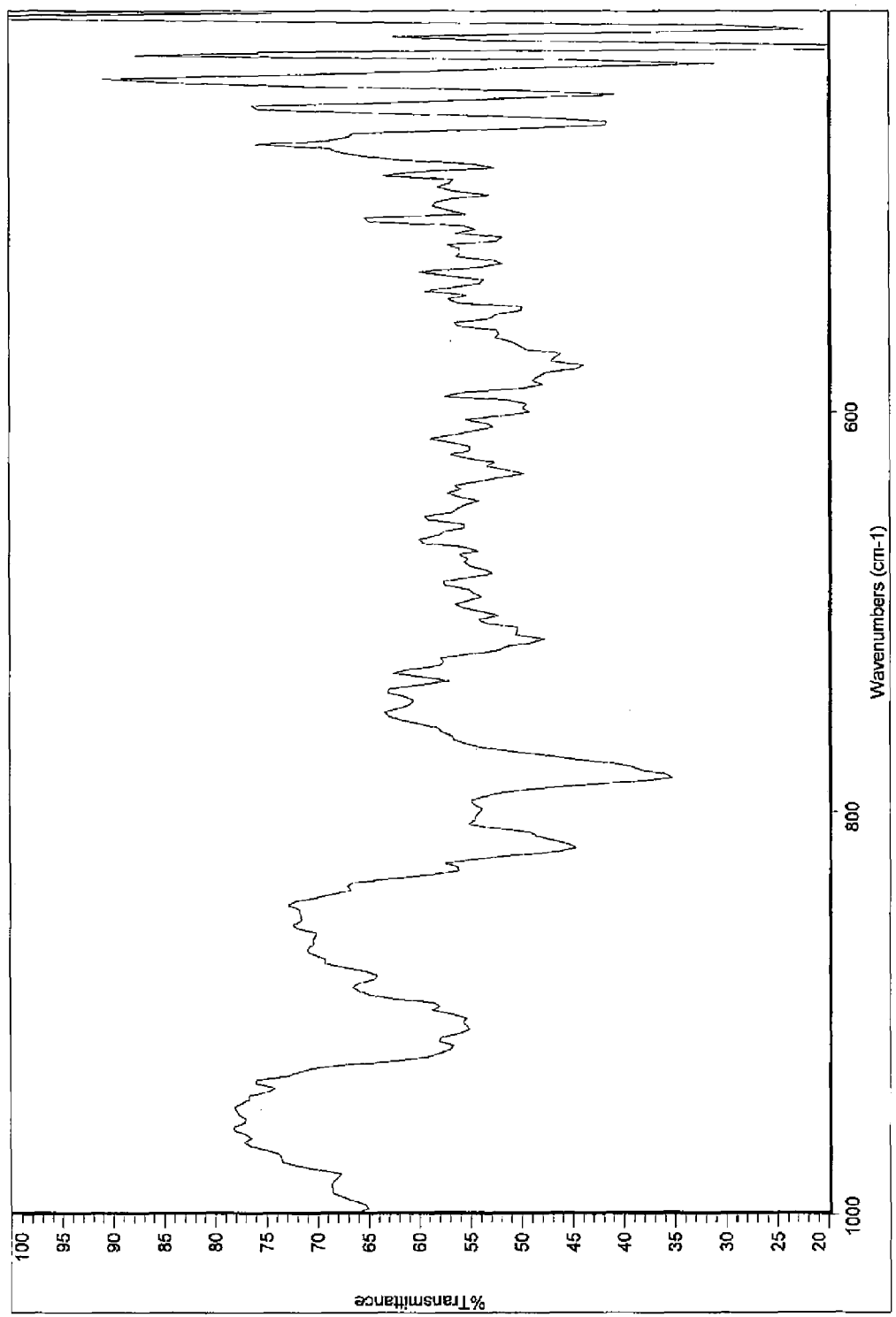

20. The crystalline Form E of claim 17 further characterized by a powder x-ray diffraction pattern as depicted in FIG. 5(a).

21. Crystalline Form F of gemcitabine base characterized by a powder x-ray diffraction pattern with peaks at about 20.8 and 27.6±0.2 degrees two-theta.

22. The crystalline Form F of claim 21 further characterized by a powder x-ray diffraction pattern with peaks at about 9.4, 11.8, 15.8, 24.3, and 30.1±0.2 degrees two-theta.

23. The crystalline Form F of claim 21 further characterized by a powder x-ray diffraction pattern with peaks at about 16.1, 16.8, 22.0, 28.2, and 33.0±0.2 degrees two-theta.

Figure 6A:
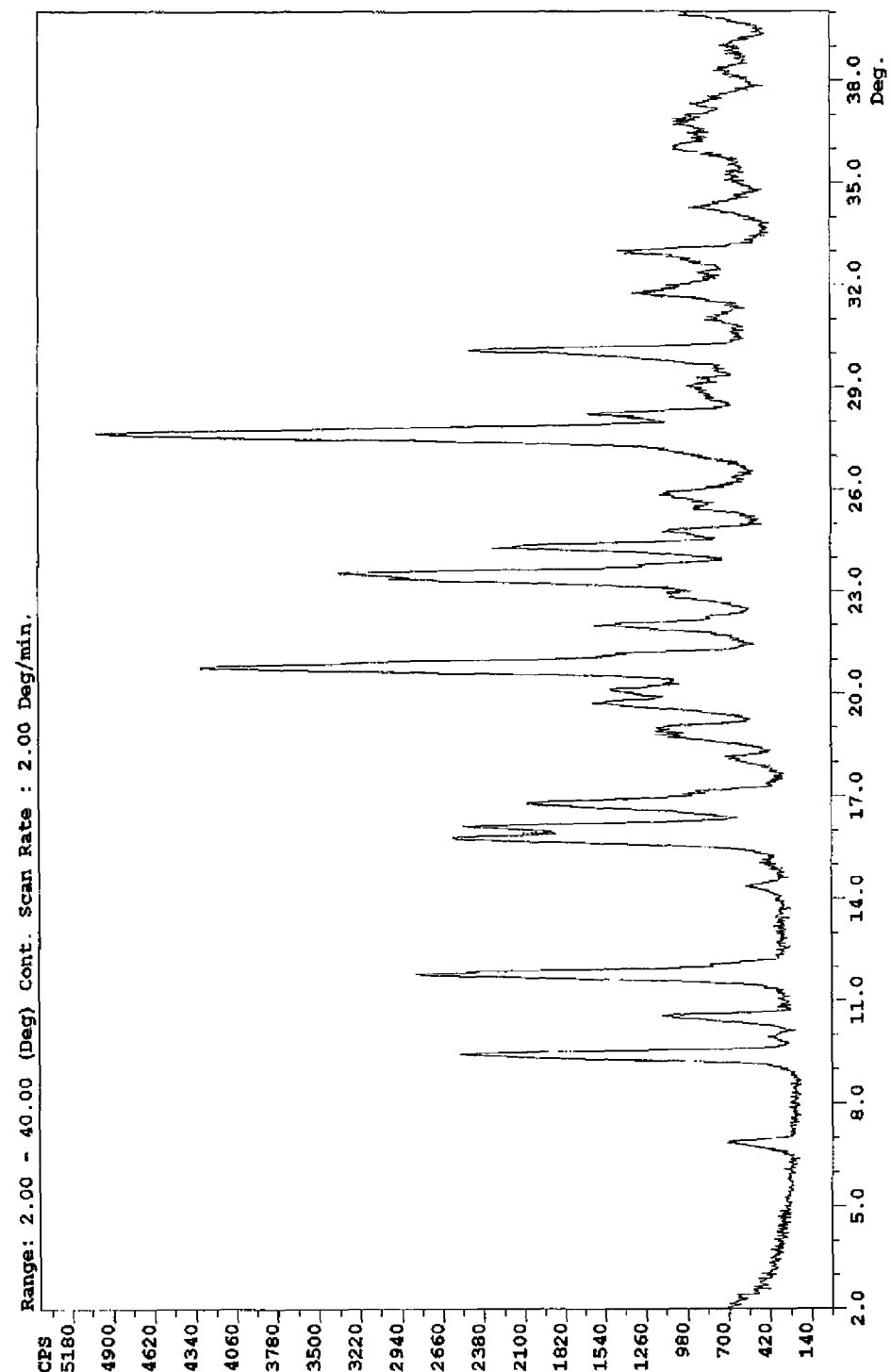
FIG. 6 is the X-ray powder diffraction pattern (a), the DSC pattern (b), and the Infrared spectrum (c) for crystalline Form F of gemcitabine base.
Figure 6A:
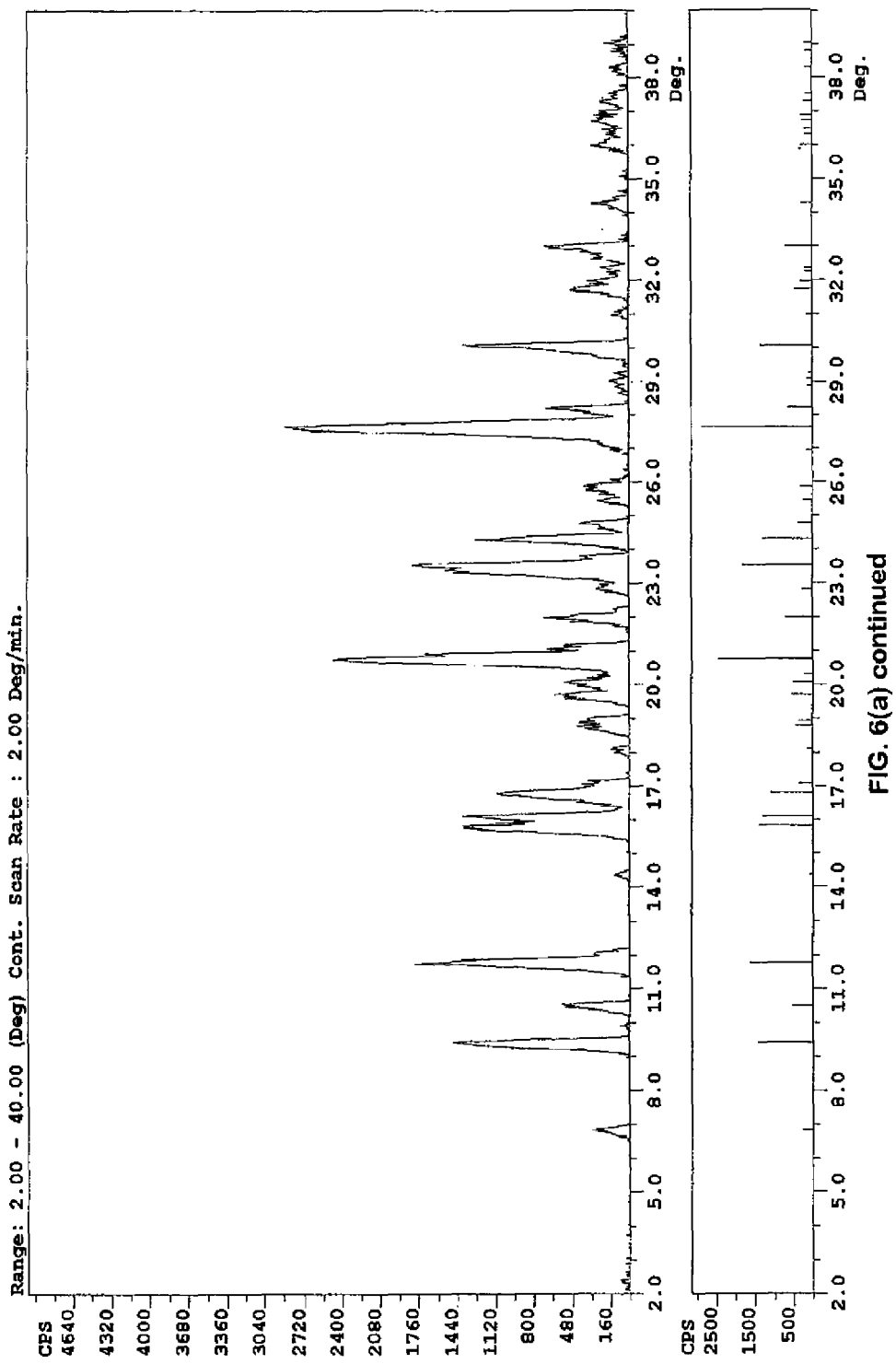
Figure 6B:
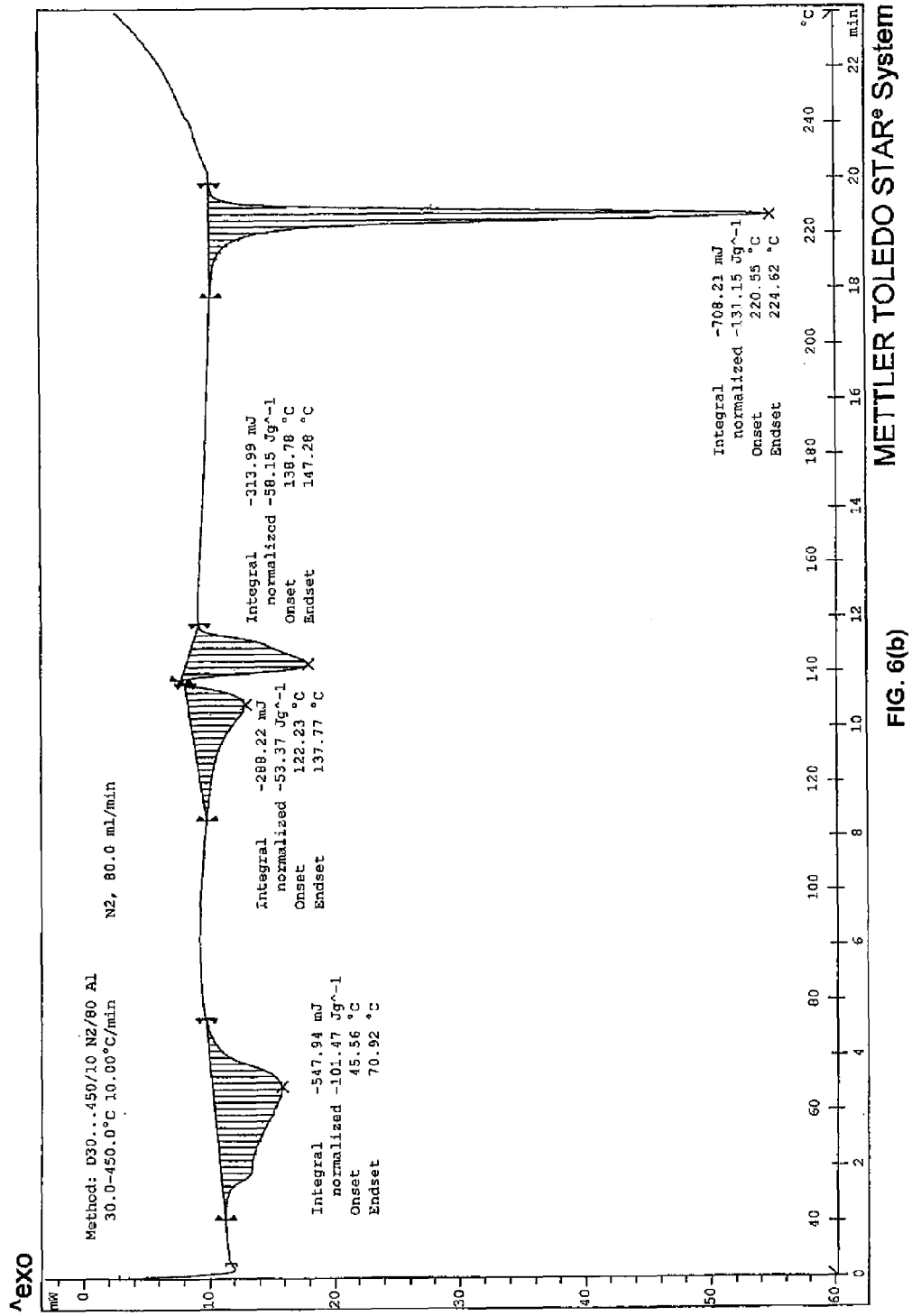
Figure 6C:
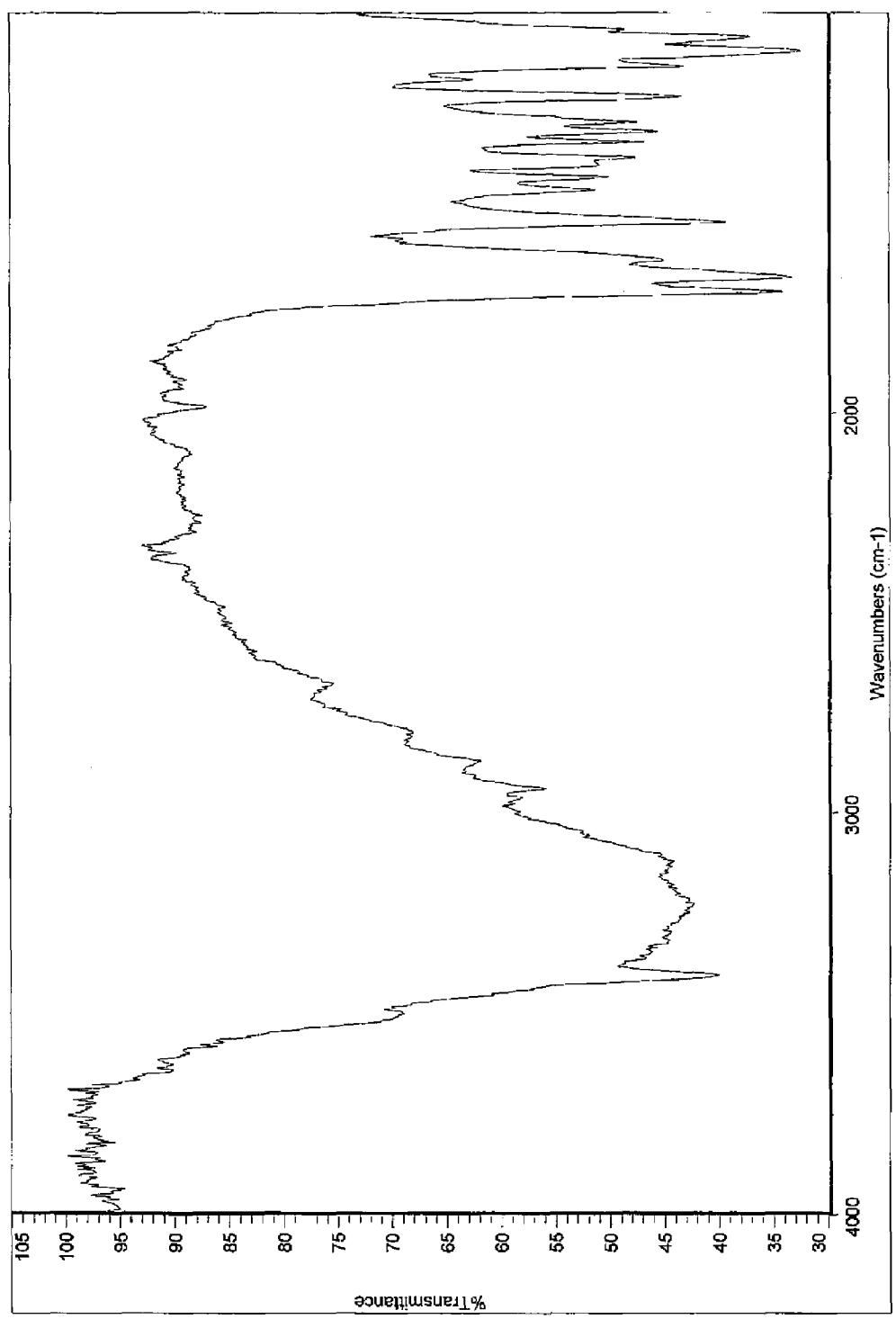
Figure 6C:
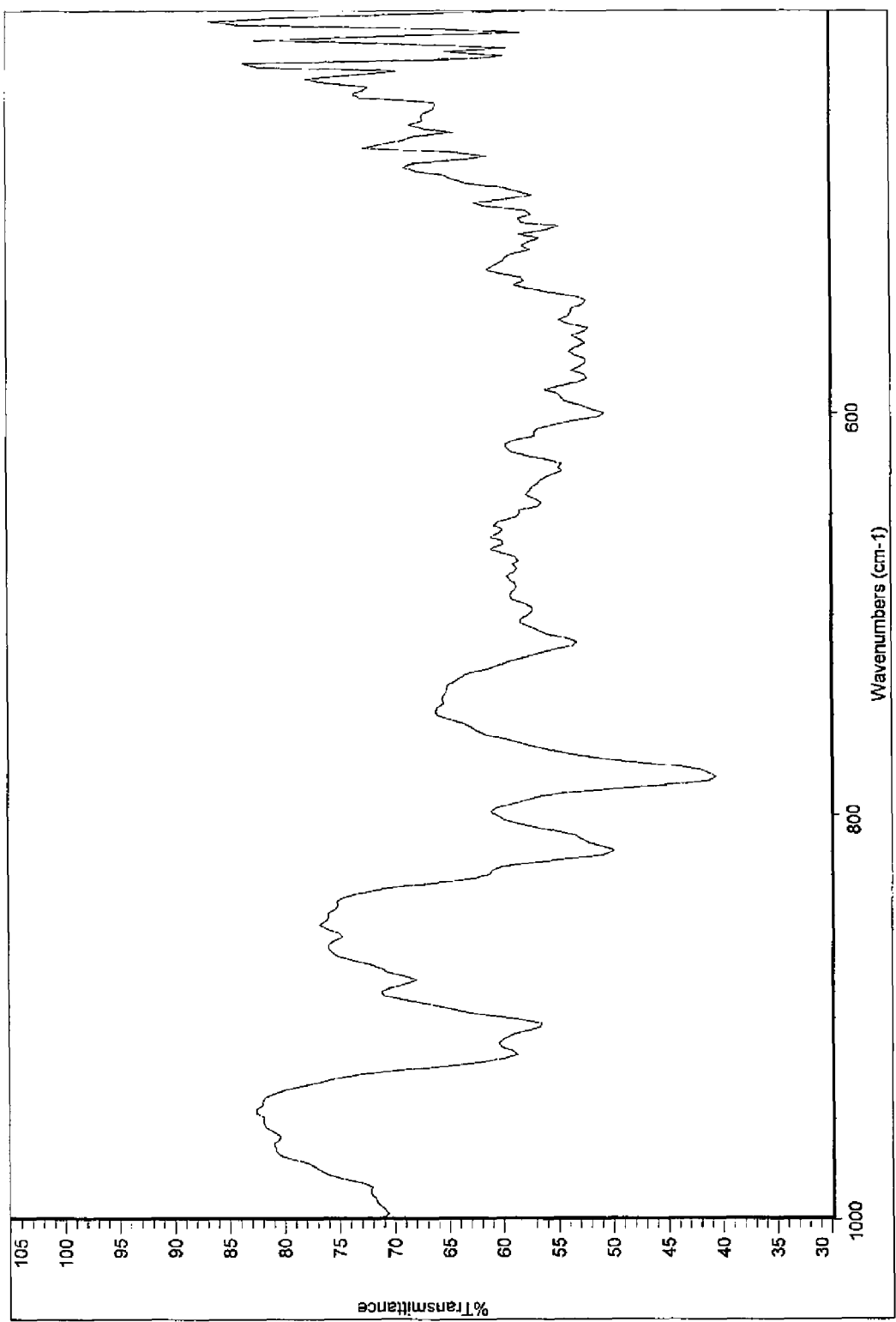

24. The crystalline Form F of claim 21 further characterized by a powder x-ray diffraction pattern as depicted in FIG. 6(a).

* * * * *